United States Patent
Porotto et al.

(10) Patent No.: US 10,172,961 B2
(45) Date of Patent: Jan. 8, 2019

(54) INHIBITORS OF FUSION BETWEEN VIRAL AND CELL MEMBRANES AS WELL AS COMPOSITIONS AND METHODS OF USING THEM

(71) Applicants: CORNELL UNIVERSITY, Ithaca, NY (US); INSERM, Paris (FR)

(72) Inventors: Matteo Porotto, New York, NY (US); Anne Moscona, New York, NY (US); Branka Horvat, Lyons (FR); Cyrille Mathieu, Lyons (FR)

(73) Assignees: Cornell University, Ithaca, NY (US); INSERM, Paris (FR)

(*) Notice: Subject to any disclaimer, the term of this patent is extended or adjusted under 35 U.S.C. 154(b) by 0 days.

(21) Appl. No.: 15/330,795

(22) PCT Filed: May 7, 2015

(86) PCT No.: PCT/US2015/029738
§ 371 (c)(1),
(2) Date: Nov. 7, 2016

(87) PCT Pub. No.: WO2015/171924
PCT Pub. Date: Nov. 12, 2015

(65) Prior Publication Data
US 2017/0216448 A1     Aug. 3, 2017

Related U.S. Application Data

(60) Provisional application No. 61/989,917, filed on May 7, 2014.

(51) Int. Cl.
| | |
|---|---|
| *A61K 47/65* | (2017.01) |
| *A61K 31/355* | (2006.01) |
| *A61K 38/16* | (2006.01) |
| *A61K 47/55* | (2017.01) |
| *A61K 47/64* | (2017.01) |
| *A61K 47/02* | (2006.01) |
| *A61K 47/10* | (2017.01) |
| *A61K 47/16* | (2006.01) |
| *A61K 47/24* | (2006.01) |
| *A61K 47/26* | (2006.01) |
| *A61K 47/42* | (2017.01) |
| *A61K 9/127* | (2006.01) |

(52) U.S. Cl.
CPC .......... *A61K 47/65* (2017.08); *A61K 31/355* (2013.01); *A61K 38/162* (2013.01); *A61K 47/551* (2017.08); *A61K 47/645* (2017.08); *A61K 9/127* (2013.01); *A61K 47/02* (2013.01); *A61K 47/10* (2013.01); *A61K 47/16* (2013.01); *A61K 47/24* (2013.01); *A61K 47/26* (2013.01); *A61K 47/42* (2013.01)

(58) Field of Classification Search
None
See application file for complete search history.

(56) References Cited

U.S. PATENT DOCUMENTS

| | | |
|---|---|---|
| 7,179,468 B1 | 2/2007 | Lu et al. |
| 8,629,101 B2 | 1/2014 | Pessi et al. |
| 2006/0229359 A1 | 10/2006 | Zhang et al. |
| 2010/0305028 A1* | 12/2010 | Pessi .................. C07K 14/005 514/3.8 |
| 2011/0318352 A1 | 12/2011 | Walensky |

OTHER PUBLICATIONS

Welsch et al., Journal of Virology, Dec. 2013, published online ahead of print on Oct. 9, 2013, 87(24):13785-13794. (Year: 2013).*
International Preliminary Report on Patentability for corresponding Application No. PCT/US2015/029738 (dated Nov. 8, 2016).
International Search Report and Written Opinion for corresponding Application No. PCT/US2015/029738 (dated Nov. 13, 2015).
Miller et al., "Inhibition of Ebola Virus Entry by a C-Peptide targeted to Endosomes," J. Biol. Chem. 286 (18):15854-15861 (2011).

* cited by examiner

*Primary Examiner* — Stacy B Chen
(74) *Attorney, Agent, or Firm* — LeClairRyan PLLC

(57) ABSTRACT

The present application relates to an inhibitor of fusion between a viral membrane from an enveloped virus and a cell membrane, where the viral membrane comprises a fusion mediating protein including a C-terminal peptide. The inhibitor comprises the C-terminal peptide of the fusion mediating protein from an enveloped virus and tocopherol or a derivative or pharmaceutically acceptable salt thereof attached to the C-terminal peptide. Also disclosed is a pharmaceutical composition including the inhibitor as well as methods of inhibiting viral fusion, blocking viral spread, and preventing or treating viral infection, with the inhibitor or pharmaceutical composition.

18 Claims, 12 Drawing Sheets
Specification includes a Sequence Listing.

VIKI-PEG$_4$-chol = Ac-VALDPIDISIVLNKIKSDLEESKEWIRRSNKILDSI-GSGSG-C(PEG$_4$-chol)-NH$_2$ (SEQ ID NO: 8)

VIKI-PEG$_4$-toc = Ac-VALDPIDISIVLNKIKSDLEESKEWIRRSNKILDSI-GSGSG-C(PEG$_4$-toc)-NH$_2$ (SEQ ID NO: 9)

VIKI-PEG$_4$-chol = Ac-VALDPIDISIVLNKIKSDLEESKEWIRRSNKILDSI-GSGSG-C(PEG$_4$-chol)-NH$_2$ (SEQ ID NO: 8)

VIKI-PEG$_4$-toc = Ac-VALDPIDISIVLNKIKSDLEESKEWIRRSNKILDSI-GSGSG-C(PEG$_4$-toc)-NH$_2$ (SEQ ID NO: 9)

Tat-Ebola-PEG₄-toc =
Ac-YGRKKRRQRRR-GSG-IEPHDWTKNITDKIDQIIHDFVDK-GSGSG-dPEG4-C-(Tocopherol) (SEQ ID NO: 27)

Tat-Ebola-PEG₄-chol =
Ac-YGRKKRRQRRR-GSG-IEPHDWTKNITDKIDQIIHDFVDK-GSGSG-dPEG4-C-(Cholesterol) (SEQ ID NO: 26)

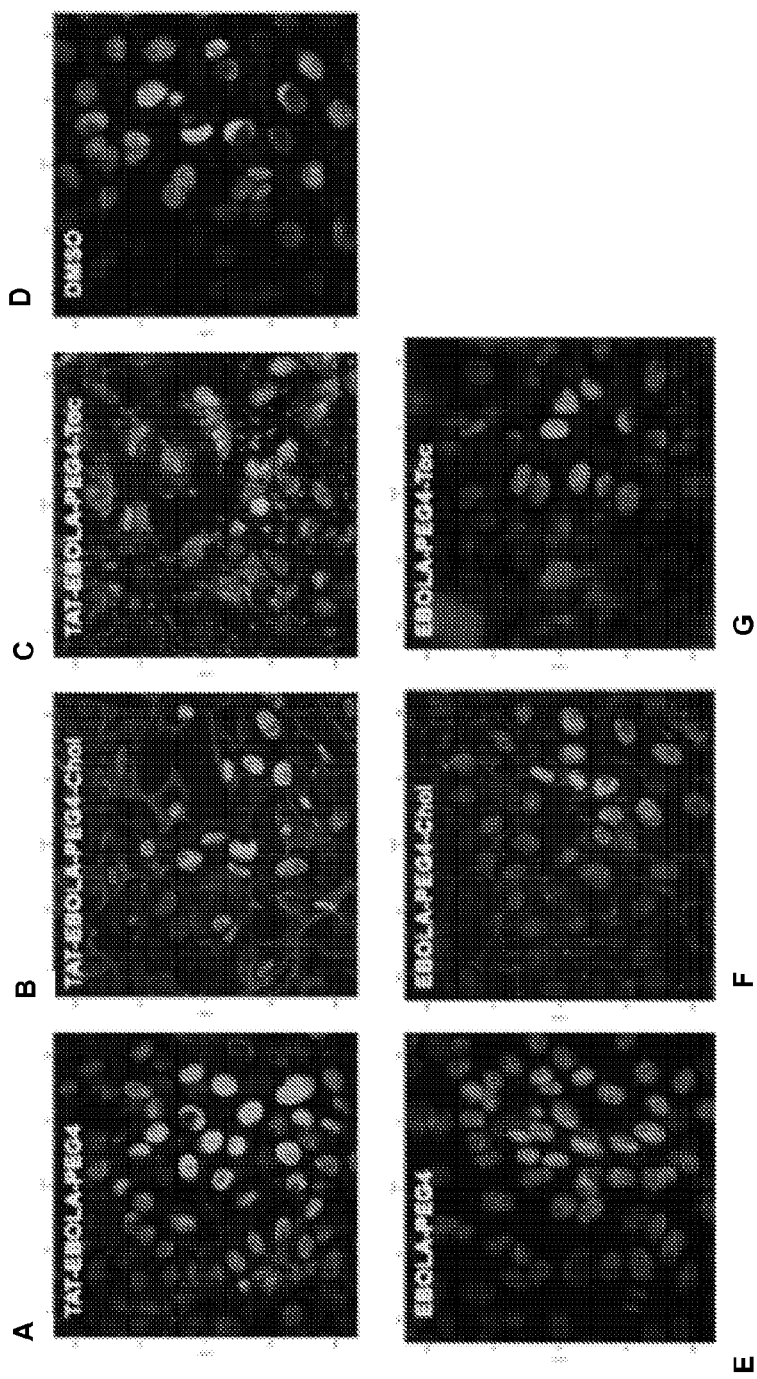
Figures 15A-G

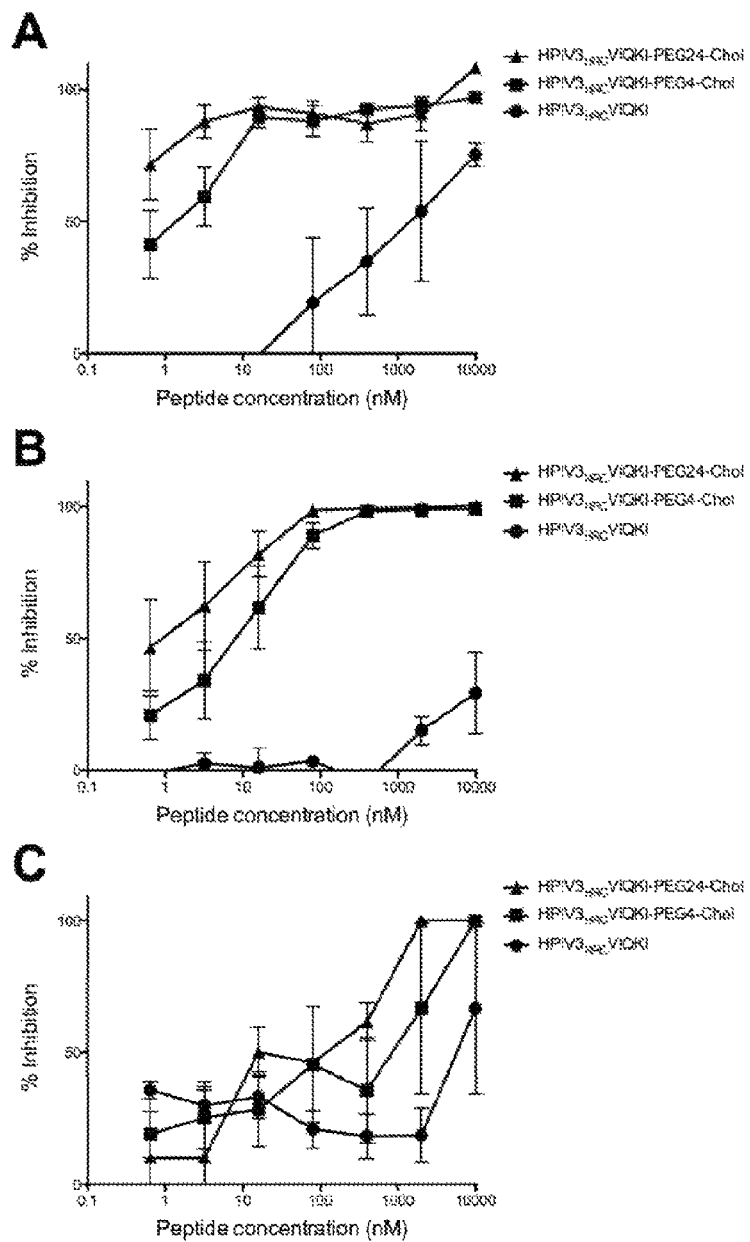
Figures 16A-C

INHIBITORS OF FUSION BETWEEN VIRAL AND CELL MEMBRANES AS WELL AS COMPOSITIONS AND METHODS OF USING THEM

This application is a national stage application under 35 U.S.C. § 371 of PCT Application No. PCT/US2015/029738, filed May 7, 2015, which claims the priority benefit of U.S. Provisional Patent Application Ser. No. 61/989,917, filed May 7, 2014, which are hereby incorporated by reference in their entirety.

This invention was made with government support under grant number NS076385 & AI101333 awarded by the National Institutes of Health. The government has certain rights in the invention.

FIELD OF THE INVENTION

The present application relates to inhibitors of fusion between viral and cell membranes as well as compositions and methods of using them.

BACKGROUND OF THE INVENTION

Fusion between the viral and target cell membranes is an obligatory step for the infectivity of all enveloped viruses, and blocking this process is a clinically validated therapeutic strategy. Viral fusion is driven by specialized proteins which, although specific to each virus, act through a common mechanism, the formation of a complex between two heptad repeat ("HR") regions. The HR regions are initially separated in an intermediate termed "prehairpin", which bridges the viral and cell membranes, and then fold onto each other to form a 6-helical bundle ("6HB"), driving the two membranes to fuse. HR-derived peptides can inhibit viral infectivity by binding to the prehairpin intermediate and preventing its transition to the 6HB. The antiviral activity of HR-derived peptides differs considerably among enveloped viruses. For weak inhibitors, potency can be increased by peptide engineering strategies, but sequence-specific optimization is time-consuming. It has been possible to increase potency without changing the native sequence, by the attachment of a cholesterol group to the HR peptide ("cholesterol-tagging") and by combining cholesterol-tagging with dimerization of the HR-derived sequence.

Many fusion inhibitors of enveloped viruses have been reported to date. To exemplify the process of such development, the generation and testing of inhibitors of the Measles virus ("MV") is reported. MV is one of the most infectious microorganisms known, and continues to cause extensive morbidity and mortality worldwide. Despite the availability of a vaccine and the measles initiative launched by WHO, UNICEF, and their partners to increase vaccine coverage, MV has not been eradicated and caused 140,000 deaths globally as recently as 2010 (Simons et al., "Assessment of the 2010 Global Measles Mortality Reduction Goal: Results from a Model of Surveillance Data," *Lancet* 379:2173-8 (2012)), making it one of the major causes of mortality among vaccine-preventable diseases. Measles cases in North America have increased in recent years, with hundreds of confirmed cases in 2011; European eradication of MV is also far behind the expected deadlines, and numerous outbreaks have occurred during the last few years (Moss et al., "Measles," *Lancet* 379:153-64 (2012) and De Serres et al., "The Largest Measles Epidemic in North America in a Decade—Quebec, Canada, 2011: Contribution of Susceptibility, Serendipity and Super-Spreading Events on Elimination," *J. Infect. Dis.* 2012)). Therefore, although vaccination is essential for the control of measles, it alone may not be sufficient (Moss et al., "Measles," *Lancet* 379:153-64 (2012) and Plemper et al., "Measles Control—Can Measles Virus Inhibitors Make a Difference?" *Curr. Opin. Invest. Drugs* 10:811-20 (2009)) and should be complemented by the use of antiviral therapy to restrict virus dissemination (Plemper et al., "Measles Control—Can Measles Virus Inhibitors Make a Difference?" *Curr. Opin. Invest. Drugs* 10:811-20 (2009)).

Complications of MV infection occur in up to 40% of cases, and those involving the Central Nervous System ("CNS") are rare but serious. Primary measles encephalitis occurs in 1-3 of 1000 infected patients, with recovery of infectious virus from the cerebrospinal fluid or brain (Hosoya, "Measles Encephalitis: Direct Viral Invasion or Autoimmune-Mediated Inflammation?" *Internal Med.* 45:841-2 (2006) and Buchanan et al., "Measles Virus and Associated Central Nervous System Sequelae," *Seminars Ped. Neurol.* 19:107-14 (2012)). Another CNS complication, acute postinfectious encephalomyelitis, also occurs during or shortly after acute measles but seems to be associated with an autoimmune etiology, and virus is not isolated. Subacute sclerosing panencephalitis ("SSPE") occurs in 4-11 of 100,000 cases of acute measles, causing progressive dementia, seizures, and ataxia (Allen et al., "The Significance of Measles Virus Antigen and Genome Distribution in the CNS in SSPE for Mechanisms of Viral Spread and Demyelination," *J. Neuropathol. Exper. Neurol.* 55:471-80 (1996)). Another form of progressive MV-induced CNS disease, known as measles inclusion body encephalitis ("MIBE"), occurs in immunosuppressed patients 1 to 6 months following measles infection, and is characterized by seizures, motor and sensory deficits, and lethargy, with either an acute or a subacute fatal course. Nonrestricted virus replication, due to an absent or decreased immune response, results in cytolytic viral replication in the brain tissue (Buchanan et al., "Measles Virus and Associated Central Nervous System Sequelae," *Seminars Ped. Neurol.* 19:107-14 (2012); Urbanska et al., "Spread of Measles Virus Through Axonal Pathways into Limbic Structures in the Brain of TAP1-/- Mice," *J. Med. Virol.* 52:362-9 (1997); and Norrby et al., "Measles Virus in the Brain," *Brain Res. Bulletin* 44:213-20 (1997)).

There are no specific therapies for these complications of CNS infection, often with lethal outcomes (Makhortova et al., "Neurokinin-1 Enables Measles Virus Trans-Synaptic Spread in Neurons," *Virology* 362:235-44 (2007); O'Donnell et al., "Blue Moon Neurovirology: The Merits of Studying Rare CNS Diseases of Viral Origin," *J. Neuroimmune Pharmacol.* 2010; Young et al., "Making it to the Synapse: Measles Virus Spread in and Among Neurons," *Curr. Top Microbiol. Immunol.* 330:3-30 (2009); and Reuter et al., "Measles Virus Infection of the CNS: Human Disease, Animal Models, and Approaches to Therapy," *Med. Microbiol. Immunol.* 2010)). Although treatment of SSPE has been attempted with a broad spectrum of anti-viral drugs, including ribavirin, interferons, and isoprinosin, complete remission has not been achieved (Moss et al., "Measles," *Lancet* 379:153-64 (2012); Plemper et al., "Measles Control—Can Measles Virus Inhibitors Make a Difference?" *Curr. Opin. Invest. Drugs* 10:811-20 (2009); Lin et al., "Prolonged Persistence of Measles Virus RNA is Characteristic of Primary Infection Dynamics," *Proc. Nat. Acad. Sci. U.S.A.* 109:14989-94 (2012); and Griffin et al., "Measles Virus, Immune Control, and Persistence," *FEMS Microbiol. Rev.*

36:649-62 (2012)). Therefore, in addition to vaccination, establishment of effective prophylactic therapies for MV CNS infection is important.

The present invention is directed to overcoming these and other deficiencies in the art.

SUMMARY OF THE INVENTION

The present application relates to an inhibitor of fusion between a viral membrane from an enveloped virus and a cell membrane, where the viral membrane comprises a fusion mediating protein including a C-terminal peptide. The inhibitor comprises the C-terminal peptide of the fusion mediating protein from an enveloped virus and tocopherol or a derivative or pharmaceutically acceptable salt thereof attached to the C-terminal peptide.

The present application further relates to a pharmaceutical composition including the inhibitor of the present invention and an adjuvant.

The present application also relates to a method of inhibiting viral fusion in a subject. The method includes selecting a subject infected with or at risk of being infected with a virus and administering to the selected subject the inhibitor or pharmaceutical composition of the present invention under conditions effective to inhibit viral fusion.

Another aspect of the present application relates to a method of blocking viral spread in a subject. The method includes selecting a subject infected with or being infected with a virus and administering to the selected subject the inhibitor or pharmaceutical composition of the present invention under conditions effective to block viral spread.

A further aspect of the present application relates to a method of preventing or treating a viral infection resulting from an enveloped virus in a subject. The method includes selecting a subject infected with or at risk of being infected with a virus and, administering to the selected subject the inhibitor or pharmaceutical composition of the present invention under conditions effective to prevent or treat a viral infection resulting from an enveloped virus.

Peptides derived from either N-terminal or C-terminal heptad repeat regions (HRN and HRC respectively) of paramyxovirus F proteins can interfere with the structural rearrangements required for fusion (Lambert et al., "Peptides from Conserved Regions of Paramyxovirus Fusion (F) Proteins are Potent Inhibitors of Viral Fusion," *Proc. Natl. Acad. Sci. U.S.A.* 93:2186-91 (1996); Yao et al., "Peptides Corresponding to the Heptad Repeat Sequence of Human Parainfluenza Virus Fusion Protein are Potent Inhibitors of Virus Infection," *Virology* 223:103-12 (1996); Baker et al., "Structural Basis for Paramyxovirus-Mediated Membrane Fusion," *Mol. Cell* 3:309-19 (1999); Wild et al., "Peptides Corresponding to a Predictive Alpha-Helical Domain of Human Immunodeficiency Virus Type 1 gp41 are Potent Inhibitors of Virus Infection," *Proc. Natl. Acad. Sci. U.S.A.* 91:9770-4 (1994); and Lu et al., "A Trimeric Structural Domain of the HIV-1 Transmembrane Glycoprotein," *Nat. Struct. Biol.* 2:1075-82 (1995), which are hereby incorporated by reference in their entirety). The current paradigm for the mechanism of HR-derived peptide action is that HRC peptides bind to the postulated extended intermediate state of F, after the fusion peptide has inserted into the target membrane, and prevent the transition to the post-fusion conformation (Harrison, "Viral Membrane Fusion," *Nat. Struct. Mol. Biol.* 15:690-8 (2008), which is hereby incorporated by reference in its entirety). The efficacy of peptide inhibition depends on both the strength of interaction of the peptide with the target fusion protein and the temporal window of access to the target sequence (Porotto et al., "Kinetic Dependence of Paramyxovirus Entry Inhibition," *J. Virol.* 83:6947-6951 (2009) and Porotto et al., "Inhibition of Nipah Virus Infection In Vivo: Targeting an Early Stage of Paramyxovirus Fusion Activation during Viral Entry," *PLoS Pathog.* 6(10)e1001168 (2010), which are hereby incorporated by reference in their entirety).

A novel method is presented to improve the efficacy and pharmacokinetics of peptide inhibitors of viral entry for enveloped viruses, by attaching tocopherol or a derivative or acceptable salt thereof to the C-terminal amino acid of peptide viral entry inhibitors. The fusogenic peptide may be directly bound to tocopherol, or a derivative thereof.

Alternatively, fusogenic peptides may be connected by a linker which comprises two or more amino acids. As described herein, linkers can comprise peptides, polyether compounds (i.e., PEG), and/or combinations thereof. A common linker is Gly-Ser-Gly ("GSG") or multiples thereof $(GSG)_n$. In applications where it is important to have longer distance between the tocopherol and the viral peptide inhibitor, polyethylene glycol ("PEG") chains of varying lengths (i.e., $(PEG)_n$) can be inserted between these two ends. The benefit of a linker is that it assists relative movement between the fusogenic peptide and the tocopherol or derivative thereof which facilitates presenting the fusogenic peptide in the correct orientation for incorporation into the HR2 helix and to disrupt viral fusion. Compared to unconjugated inhibitors or inhibitors conjugated with other lipids, the inhibitors of the present invention are more effective in vitro, have more favorable pharmacokinetics, and demonstrated in vivo efficacy.

To evaluate the efficiency of tocopherol conjugated peptides in the MV infection a transgenic mouse model expressing human SLAM was used in an interferon receptor deficient background. MV infection in these mice led to the development of an acute neurological syndrome characterized by lethargy, seizures, ataxia, weight loss, and death (Sellin et al., "High Pathogenicity of Wild-Type Measles Virus Infection in CD150 (SLAM) Transgenic Mice," *J. Virol.* 80:6420-9 (2006) and Sellin et al., "Current Animal Models: Transgenic Animal Models for the Study of Measles Pathogenesis," *Curr. Top Microbiol. Immunol.* 330: 111-27 (2009), both of which are hereby incorporated by reference in their entirety). This model, in allowing a simple readout of the efficacy of an anti-viral treatment, provides an accurate experimental means to test novel anti-MV preventive and therapeutic strategies (Sellin et al., "High Pathogenicity of Wild-Type Measles Virus Infection in CD150 (SLAM) Transgenic Mice," *J. Virol.* 80:6420-9 (2006) and Sellin et al., "Current Animal Models: Transgenic Animal Models for the Study of Measles Pathogenesis," *Curr. Top Microbiol. Immunol.* 330:111-27 (2009), both of which are hereby incorporated by reference in their entirety). The study was designed to establish proof of concept for the utilization of tocopherol conjugated peptides in the prevention and treatment of measles neurological complications both in non-vaccinated or immunodepressed people.

BRIEF DESCRIPTION OF THE DRAWINGS

FIGS. 1B-1F show the schematic representations of MV HRC 2 (FIG. 1B), MV HRC 3 (FIG. 1C), MV HRC 4 (FIG. 1D), MV HRC 5 (FIG. 1E), and MV HRC 6 (FIG. 1F). The peptides consist of the MV HRC (amino acids 450-485 of MV F with a GSGSG spacer. FIGS. 1C, 1D, and 1F illustrate dimerized MV HRCs. The peptides were further modified by cholesterol conjugation (FIGS. 1B, 1D) or tocopherol conjugation (FIGS. 1E, 1F).

FIG. 2A shows the inhibition of MV entry by MV HRC peptides. Vero-SLAM cell monolayers were infected with wild type MV G954 in the presence MV HRC peptides at the indicated peptide concentrations. Viral entry was assessed by plaque reduction assay. Results are presented as percent reduction (y-axis) in plaque number compared in the absence of treatment, as a function of compound concentration (x-axis). Each point represents the mean (±standard error) of four experiments. FIG. 2B shows the inhibition of MV spread by MV HRC peptides. Vero-SLAM cell monolayers were infected with wild type MV-IC323-EGFP. After 90 minutes, medium with the indicated peptide concentrations was added. Viral spread was assessed by using a fluorescent readout of the EGFP after 72 hours. Results are presented as percent reduction in fluorescence (y-axis) compared with no treatment, as a function of compound concentration (x-axis). Each point represents the mean (±standard deviation) of a representative experiment.

FIG. 3 shows the inhibition of cell fusion. Fusion of MV H/F-co-expressing cells with SLAM bearing cells in the presence of different compound concentrations was quantitated at 6 h using a β-galactosidase complementation assay. Results are presented as percent reduction in luminescence (y-axis) compared with no treatment, as a function of compound concentration (x-axis). Each point is the mean (±standard error) of results from 3 experiments.

FIG. 4 shows that MV HRC 4 protects SLAMxIF-NARKO adult mice from the lethal MV encephalitis. Mice received the intranasal challenge of MV G954 24 h after single MV-HRC peptide intranasal treatment, as described in methods and were followed for 3 weeks p.i. Controls animals (mock) received the vehicle alone.

FIG. 7 shows a comparison of tocopherol and cholesterol conjugated peptides as therapeutic treatments against NiV infection. 8 week old Syrian golden hamsters were treated by daily intraperitoneal (i.p.) injections of indicated peptides (2 mg/kg) from the day 1 to day 10 post infection with NiV (500LD50, i.p.). Mock were injected with vehicle used to dissolve peptides. Survival was observed only in the group treated with tocopherol conjugated peptide.

FIG. 8 shows a comparison of tocopherol conjugated peptides (SEQ ID NO: 27) and cholesterol conjugated (SEQ ID NO: 26) peptides as a prophylactic treatment against Ebola virus. 5-6 week old BALB/c mice were daily treated by intraperitoneal (i.p.) injections of indicated peptides (10 mg/kg) from the day prior to day 15 post infection with 1000LD$_{50}$ of Ebola virus mouse adapted Zaire strain (ZE-BOV, i.p.). Tocopherol conjugation significantly improved peptide ability to protect from EBOV infection.

FIG. 9 shows the efficacy of peptide inhibitors against NiV with different spacers between the NiV fusion inhibiting peptide and the attached membrane anchor. Antiviral efficacy of NiV fusion inhibiting peptides with different sized linkages to cholesterol is measured in a plaque assay.

FIGS. 10A-10B show peptide staining in the brain of mice injected with VIKI-PEG4-Cholesterol (FIG. 10A) or VIKI-PEG4-Tocopherol (FIG. 10B).

FIGS. 11A-11B show peptide immunostaining in the brain of mice injected with VIKI-PEG4-Cholesterol (FIG. 11A) or VIKI-PEG4-Tocopherol (FIG. 11B). Nuclei were stained with DAPI.

FIG. 12 shows that intranasal administration of tocopherol conjugated peptide protect hamsters against NiV infection.

FIGS. 15A-G show the intracellular localization of TAT and lipid-conjugated peptides. Anti-EBOLA HRC antibodies are stained with fluorescent dye. DAPI Nuclei are stained with DAPI. FIG. 15A shows TAT-EBOLA-PEG4, FIG. 15B shows TAT-EBOLA-PEG4-Chol, FIG. 15C shows TAT-EBOLA-PEG4-Toc, FIG. 15D shows DMSO, FIG. 15E shows EBOLA-PEG4, FIG. 15F shows EBOLA-PEG4-Chol, and FIG. 15G shows EBOLA-PEG4-Toc.

FIGS. 16A-C show inhibition of envelope glycoprotein-mediated fusion by VIQKI peptides. FIG. 16A shows cells expressing HPIV3 FIN and F, FIG. 16B shows cells expressing NiV G and F, and FIG. 16C shows cells expressing RSV F. In each case, cells were allowed to fuse 293T cells in the presence of increasing concentrations of VIQKI-PEG24-chol (triangles), VIQKI-PEG4-chol (squares) or VIQKI-untagged (circles) peptides. After 4 hours, the amount of fusion was quantitated using a beta-galactosidase complementation assay. The percent inhibition of fusion (compared to results for control cells not treated with peptide) is shown as a function of the (log-scale) concentration of peptide. Values are means (±SD) of results from three experiments.

DETAILED DESCRIPTION OF THE INVENTION

Figures 1A, 1B, 1C, 1D, 1E, 1F:
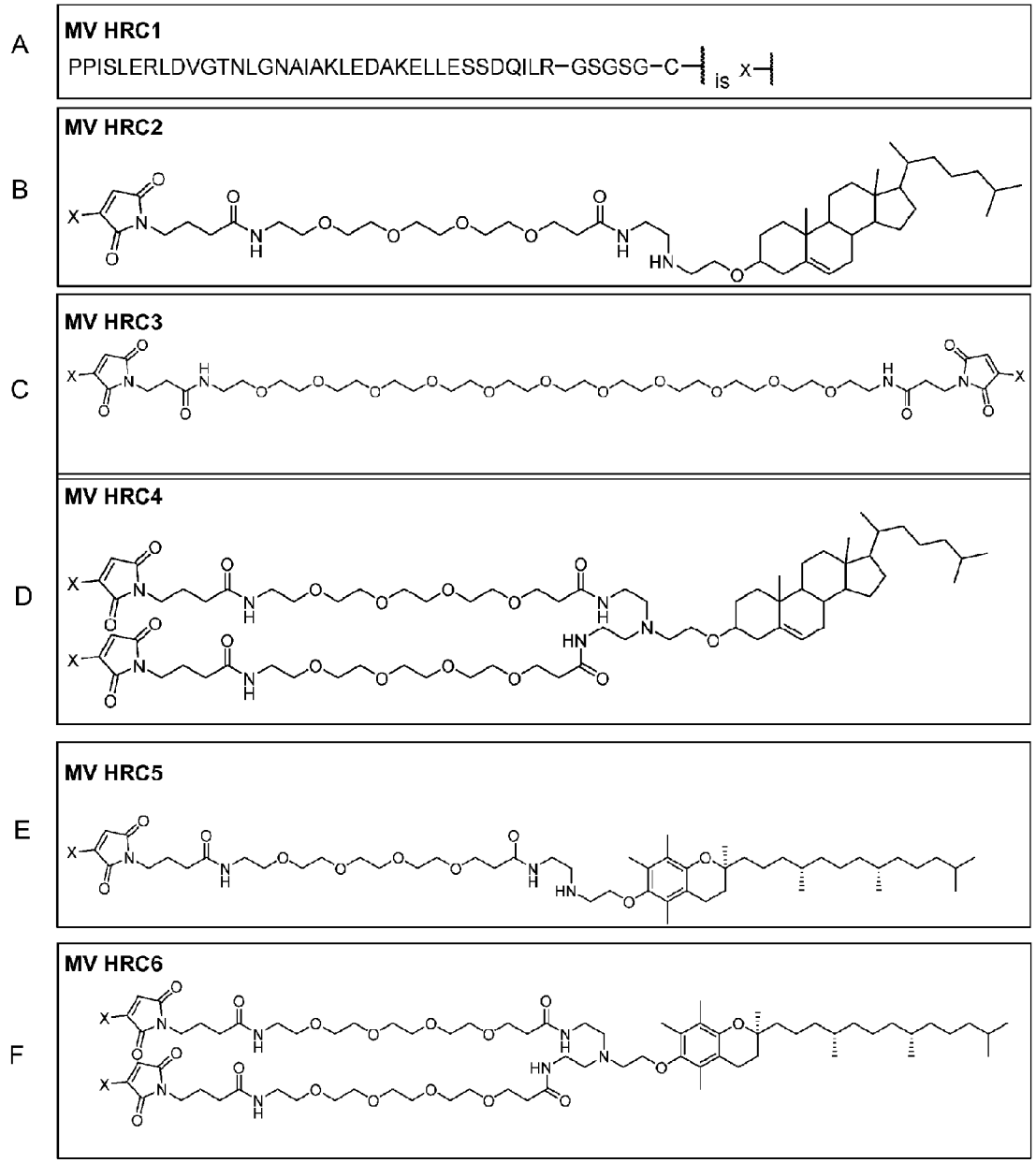
FIGS. 1A-1F are amino acid sequences and schematic representations of the measles virus ("MV") HRC Peptides. The amino acid sequence of MV HRC 1 is shown in FIG. 1A (SEQ ID NO: 1).

A first aspect of the present invention relates to an inhibitor of fusion between a viral membrane from an enveloped virus and a cell membrane, where the viral membrane comprises a fusion mediating protein including a C-terminal peptide. The inhibitor comprises the C-terminal peptide of the fusion mediating protein from an enveloped virus and tocopherol or a derivative or pharmaceutically acceptable salt thereof attached to the C-terminal peptide.

The inhibitor of fusion described herein comprises the C-terminal peptide of a fusion mediating protein from an enveloped virus. An enveloped virus is any virus in which a nucleoprotein core is surrounded by a lipoprotein envelope having a closed bilayer of lipid derived from that of the host cell's membrane(s), with glycoprotein on the outside and matrix protein or nucleocapsid protein on the inside. Exemplary enveloped virus families include Togaviridae, Flaviviridae, Coronaviridae, Rhabdoviridae, Filoviridae, Paramyxoviridae, Orthomyxoviridae, Bunyaviridae, Arenaviridae, Retroviridae, Herpesviridae, Poxviridae and Iridoviridae. These viruses and others are responsible for such diseases as encephalitis, intestinal infections, immunosuppressive disease, respiratory disease, hepatitis, and pox infections.

As described herein, fusion of enveloped viruses with the host cell is a key step in viral infectivity. The fusion process during viral entry is driven by specialized proteins that undergo a series of conformational changes to bring the viral and host membranes together and promote formation of a fusion pore (Eckert et al., "Mechanisms of Viral Membrane Fusion and its Inhibition," *Annu. Rev. Biochem.* 70:777-810 (2001), which is hereby incorporated by reference in its entirety).

Paramyxoviruses include several important human pathogens including, without limitation, measles virus ("MV"), respiratory syncytial virus ("RSV"), parainfluenza virus ("PIV"), Nipah virus ("NiV"), Hendra virus, Sendai virus, Newcastle disease virus ("NDV"), and mumps virus. Paramyxoviruses possess two envelope glycoproteins directly involved in viral entry and pathogenesis: a fusion protein ("F") and a receptor-binding protein (HN for the parainfluenza viruses, H for MV, or G for HeV and NiV). The MV F protein, like other paramyxovirus F proteins belonging to the group of "class I" fusion proteins (Weissenhorn et al., "Virus Membrane Fusion," *FEBS Lett.* 581: 2150-5 (2007) and White, "The First Family of Cell-Cell Fusion," *Dev. Cell* 12:667-8 (2007), which are hereby incorporated by reference in their entirety), is synthesized as a precursor protein that is proteolytically processed post-translationally to form a trimer of disulfide-linked heterodimers. This cleavage event exposes a new N-terminus, called the fusion peptide, which is essential for membrane fusion activity. MV fuses with cell membranes at the cell surface. The H protein binds to cellular surface receptors, and activates the viral F protein to undergo the required conformational changes leading to fusion. During the structural rearrangements of F, the protein transiently passes through an extended intermediate form, and inserts the fusion peptide into the target membrane, before refolding upon itself to attain the post-fusion conformation in a series of steps that drive membrane merger (Weissenhorn et al., "Virus Membrane Fusion," *FEBS Lett.* 581:2150-5 (2007) and White, "The First Family of Cell-Cell Fusion," *Dev. Cell* 12:667-8 (2007), which are hereby incorporated by reference in their entirety).

Retroviruses include, without limitation, alpharetrovirus, betaretrovirus, gammaretrovirus, deltaretrovirus, epsilonretrovirus, lentivirus, and spumavirus. Exemplary lentiviruses include human immunodeficiency virus ("HIV"), simian immunodeficiency virus ("SIV"), feline immunodeficiency virus ("FIV"), puma lentivirus, equine infectious anemia, bovine immunodeficiency virus ("BIV"), caprine arthritis encephalitis virus, and visna virus. The HIV-1 envelope glycoprotein mediates the fusion of viral and target cell membranes, the first critical step leading to infection. The precursor of the envelope protein, gp160, forms a trimer and is then cleaved by a furin-like protease into two non-covalently associated fragments: gp120 for receptor binding and gp41 for membrane fusion. Three copies of each fragment make up the mature envelope spike $(gp120/gp41)_3$. This trimeric complex undergoes large, irreversible structural rearrangements after binding to the primary receptor CD4 and coreceptor (e.g., CCR5 and CXCR4) and drives the membrane fusion process (Kovacs et al., "HIV-1 Envelope Trimer Elicits more Potent Neutralizing Antibody Responses than Monomeric gp120," *PNAS* 9(30): 12111-6 (2012), which is hereby incorporated by reference in its entirety).

Filoviruses include, without limitation, Cuevavirus, Ebola virus, and Marburg virus. Exemplary Ebola viruses include Bundibugyo virus ("BEBOV"), Reston virus ("REBOV"), Sudan virus ("SEBOV"), Taï Forest virus ("CIEBOV"), and Ebola virus Zaire ("ZEBOV"). Filoviruses mediate receptor binding and fusion through GP1 and GP2, respectively. As a class I viral fusion protein, $GP_{1,2}$ exists as a trimer of GP1 and GP2 heterodimeric subunits and is found in its full-length, heavily glycosylated, pre-fusion form on the surface of newly budded virions. This pre-fusion class I glycoprotein conformation is thought to be a metastable state, that upon the appropriate set of triggers, will convert to its post-fusion, low-energy form (White et al., "Structures and Mechanisms of Viral Membrane Fusion Proteins: Multiple Variations on a Common Theme," *Crit. Rev. Biochem. Mol. Biol.* 43: 189-219 (2008), which is hereby incorporated by reference in its entirety).

Orthomyxoviruses include, without limitation, influenza virus A, Influenza virus B, Influenza virus C, Isavirus, Thogotovirus, and Dhori virus. Exemplary Influenza A viruses include H1N1, H1N2, H2N2, H3N1, H3N2, H3N8, H5N1, H5N2, H5N3, H5N8, H5N9, H7N1, H7N2, H7N3, H7N4, H7N7, H7N9, H9N2, and H10N7. Hemagglutinin 2 ("HA2") of influenza virus, an orthomyxovirus, is the prototypic RNA virus Class I fusion protein and contains an amino terminal hydrophobic domain, referred to as the fusion peptide, that is exposed during cleavage of the hemagglutinin precursor protein. The membrane fusion proteins of RNA viruses from several diverse families, including arenaviruses, coronaviruses, filoviruses, orthomyxoviruses, paramyxoviruses, and retroviruses, share several common structural features with HA2 and have been referred to as Class I viral fusion proteins.

MV belongs to the Paramyxoviridae family, and its lipid envelope carries the two glycoproteins directly involved in viral entry and pathogenesis: a fusion protein (F) and a receptor-binding protein (H). The MV fusion (F) protein, like other paramyxovirus F proteins belonging to the group of "class I" fusion proteins (Weissenhorn et al., "Virus Membrane Fusion," *FEBS Lett.* 581:2150-5 (2007) and White, "The First Family of Cell-Cell Fusion," *Dev. Cell* 12:667-8 (2007), which are hereby incorporated by reference in their entirety), is synthesized as a precursor protein that is proteolytically processed postranslationally to form a trimer of disulfide-linked heterodimers. This cleavage event exposes a new N-terminus, called the fusion peptide, which is essential for membrane fusion activity. MV fuses with cell membranes at the cell surface. The receptor-binding protein (H) binds to cellular surface receptors, and activates the viral F protein to undergo the required conformational changes leading to fusion. During the structural rearrangements of F, the protein transiently passes through an extended intermediate form, and inserts the fusion peptide into the target membrane, before refolding upon itself to attain the post-fusion conformation in a series of steps that drive membrane merger (Weissenhorn et al., "Virus Membrane Fusion," *FEBS Lett.* 581:2150-5 (2007) and White, "The First Family of Cell-Cell Fusion," *Dev. Cell* 12:667-8 (2007), which are hereby incorporated by reference in their entirety).

The peptides of the present invention can be synthesized using standard peptide synthesis operations. These include but are not limited to 9-Fluorenylmethyloxy-carbonyl ("FMOC") synthesis protocols that can be carried out on automated solid phase peptide synthesis instruments including, without limitation, the Applied Biosystems 431A, 433A synthesizers and Peptide Technologies Symphony or large scale Sonata or CEM Liberty automated solid phase peptide synthesizers. This can be followed with standard HPLC purification to achieve a purified peptide product.

In general, thiol groups present in cysteine (or cysteine derivative) side chains can be reacted with reagents possessing thiol-reactive functional groups using known reaction schemes. Exemplary thiol-reactive functional groups include, without limitation, iodoacetamides, maleimides, and alkyl halides. Reagents to be conjugated include those listed above.

The Paramyxovirus F protein, the HIV and SIV gp160, Ebola virus GP, and influenza virus HA proteins all form homotrimers that must by proteolytically cleaved to be biologically active. The resulting TM domain-containing subunits contain a hydrophobic fusion peptide at the new N-termini, which has been shown to insert into the target membrane during the fusion process.

For viruses that fuse with cell membranes at the cell surface, like HPIV, HeV, and NiV, the receptor-binding protein binds to cellular surface receptors, brings the viral envelope in proximity to the plasma membrane, and activates the viral F protein to undergo the required conformational changes leading to fusion. Receptor-ligand interaction is required for the paramyxovirus F protein to undergo the series of steps that lead to fusion (Porotto et al., "Triggering of Human Parainfluenza Virus 3 Fusion Protein(F) by the Hemagglutinin-Neuraminidase (HN); An HN Mutation Diminishing the Rate of F Activiation and Fusion," *J. Virol.* 77:3647-3654 (2003); Porotto et al., "Influence of the Human Parainfluenza Virus 3 Attachment Protein's Neuraminidse Activity on its Capacity to Activate the Fusion Protein," *J. Virol.* 79:2383-2392 (2005); and Moscona et al., "Fusion Properties of Cells Persistently Infected with Human Parainfluenza Virus Type 3: Participation of Hemagglutinin-Neuraminidase in Membrane Fusion," *J. Virol.* 65:2773-2777 (1991), which are hereby incorporated by reference in their entirety).

As described above, peptides derived from either N-terminal or C-terminal regions (e.g., paramyxovirus HRN and HRC) of envelope virus fusion proteins can interfere with the structural rearrangements required for fusion. For example, the HRN-binding peptide T20 has been approved for the treatment of HIV infection (Matthews et al., "Enfuvirtide: the First Therapy to Inhibit the Entry of HIV-1 into Host CD4 Lymphocytes," *Nat. Rev. Drug Discov.* 3: 215-25 (2004), which is hereby incorporated by reference in its entirety). In some embodiments, the C-terminal peptide is an HRC peptide. In other embodiments, the HRC peptide is derived from a virus selected from the group consisting of Measles virus, Ebola virus, Human parainfluenza virus, Nipah virus, and HIV-1. One example of a peptide useful in the present invention is PPISLERLDVGTNLGNAIAKLEDAKELLESSDQILR (SEQ ID NO: 38).

As described above, the paramyxovirus F protein, the HIV and SIV gp160, Ebola virus GP, and influenza virus HA proteins belongs to the group of "class I" fusion proteins (Weissenhorn et al., "Virus Membrane Fusion," *FEBS Lett* 581: 2150-2155 (2007) and White et al., "The First Family of Cell-Cell Fusion," *Dev. Cell* 12: 667-668 (2007), which are hereby incorporated by reference in their entirety). In one embodiment, the C-terminal peptide is a Type I viral fusogenic peptide. An exemplary C-terminal peptide of the invention includes, but is not limited to, MV HRC1:

```
                                    (SEQ ID NO: 1)
PPISLERLDVGTNLGNAIAKLEDAKELLESSDQILR-GSGSG-C.
```

As described herein, tocopherols constitute a series of related benzopyranols (or methyl tocols) that occur in plant tissues and vegetable oils and are powerful lipid-soluble antioxidants. In the tocopherols, the $C_{16}$ side chain is saturated, and in the tocotrienols it contains three trans double bonds. Together, these two groups are termed the tocochromanols. In essence, the tocopherols have a 20-carbon phytyl tail (including the pyranol ring), with variable numbers of methyl groups attached to the benzene ring, and the tocotrienols a 20-carbon geranylgeranyl tail with double bonds at the 3', 7' and 11' positions, attached to the benzene ring. The side-chain methyl groups of natural tocopherols have R,R,R stereochemistry. The four main constituents of the two classes are termed—alpha (5,7,8-trimethyl), beta (5,8-dimethyl), gamma (7,8-dimethyl) and delta (8-methyl). The tocotrienols have a single chiral center.

These compounds are produced by plants and other oxygenic photosynthetic organisms, such as algae and some cyanobacteria, and are essential components of the diet of animals, and collectively they are termed "vitamin E." Tocopherols are present in all photosynthetic organisms, but the tocotrienols are found only in certain plant families. In general, tocotrienols tend to be abundant only in seeds and fruits, especially of monocots such as wheat, rice, and barley, though a major commercial source is palm oil. In leaf tissue, α-tocopherol is often the main isomer, while γ-tocopherol is the primary tocopherol of many seeds.

The mechanism of biosynthesis of tocopherols is well understood, and involves coupling of phytyl diphosphate with homogentisic acid (2,5-dihydroxyphenylacetic acid), followed by cyclization and methylation reactions.

The inhibitor of the present invention includes tocopherol, a tocopherol derivative, or pharmaceutically acceptable salt thereof. Examples of tocopherol that may be used in the present aspect include, but are not limited to, alpha-tocopherol, beta-tocopherol, gamma-tocopherol, and delta-tocopherol. Examples of useful tocopherol derivatives or pharmaceutically acceptable salts thereof can be selected from the group consisting of, but is by no means limited to, tocotrienols, tocopheroxyl radical, 8α-alkyldi oxytocopherone, tocopherol quinone, tocopherol hydroquinone, d,l-tocopherol, d,l-tocopheryl acetate, alpha-tocopheryl acetate, alpha-tocopheryl nicotinate, and alpha-tocopheryl succinate. The C-terminal peptide is covalently or non-covalently bound to the tocopherol or derivative or pharmaceutically acceptable salt thereof.

In some embodiments, the C-terminal peptide is a monomer. In other embodiments, the C-terminal peptide is dimerized.

In alternate embodiments, the inhibitor may further comprise a linker coupling the C-terminal peptide and the tocopherol or the derivative or the pharmaceutically acceptable salt thereof. In accordance with this aspect of the present invention, linkers may be selected from the group consisting of a peptide of two or more amino acids and one or more polyethylene glycol oligomer moieties.

Polyethylene glycol ("PEG") is a typically biologically inert, non-immunogenic chemical that confers greater water solubility to peptides with which it is incorporated as constituent chemical group. PEG is non-toxic and non-immunogenic, hydrophilic, and highly flexible. In some embodiments, the linker may comprise one or more Gly-Ser-Gly ("GSG") moieties. In additional embodiments, the linker comprises one or more polyethylene glycol oligomer moieties having a formula of —(OCH$_2$CH$_2$)m-, wherein m is an integer 1 to 24. In one embodiment, m is 4.

Linkers may include synthetic sequences of amino acids that are commonly used to physically connect polypeptide domains to each other or to biologically relevant moieties. Most linker peptides are composed of repetitive modules of one or more of the amino acids glycine and serine. Peptide linkers have been well-characterized and shown to adopt unstructured, flexible conformations. For example, linkers comprised of Gly and Ser amino acids have been found to not interfere with assembly and binding activity of the domains it connects. (Freund et al., "Characterization of the Linker Peptide of the Single-chain Fv Fragment of an Antibody by NMR Spectroscopy," *FEBS* 320:97 (1993), which is hereby incorporated by reference in its entirety).

As described herein, PEG has been found to act not only to facilitate the C-terminal peptide fusion to the tocopherol or a derivative or pharmaceutically acceptable salt therefore, but to also act as a buffer to prevent or reduce any interaction of the C-terminal peptide fusion to the tocopherol or a derivative or pharmaceutically acceptable salt therefore or, indeed, with any other biological compounds to which it may become exposed during the use of the fusion conjugate. Thus, the polyethylene glycol has a dual function, the first being that of a linking group facilitating the attachment of the C-terminal peptide fusion to the tocopherol or a derivative or pharmaceutically acceptable salt therefore, and the second being that of maintaining, to the greatest extent possible, a particular conformation of the C-terminal peptide fusion. The use of the PEG attachment methodology to provide a PEG linker will facilitate the binding of ligands or molecules to the C-terminal peptide, help to retain the native properties of the bound substituents (i.e., the tocopherol or a derivative or pharmaceutically acceptable salt therefore); and enhance mobility, and thus accessibility, of the attached substituents. Further, the specificity of bonding to the substituent (s) is enhanced, because the PEG linker provides a "barrier" to reduce the non-specific binding of other species to the C-terminal peptide.

The PEG utilized must be of a sufficient size to convey the desired properties, but not so large as to significantly hinder the kinetics of derivitization, attachment of the substituent, or the functionality of the attached substituent. In general, a molecular weight of 1,000-5,000, more preferably 2,000-3,000, and even more preferably 2,000 would be used, but it is to be understood that PEG polymers of even higher and/or lower molecular weights can be used depending on the particular application.

Exemplary inhibitors of the present invention include, without limitation, MV HRC2, which is shown below:

MV HRC3, which is shown below:

MV HRC4, which is shown below:

MV HRC5, which is shown below:

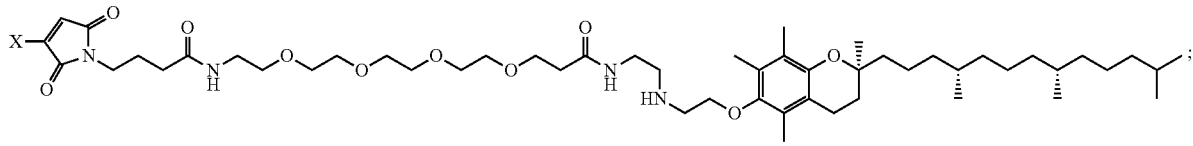

and MV HRC6, which is shown below:

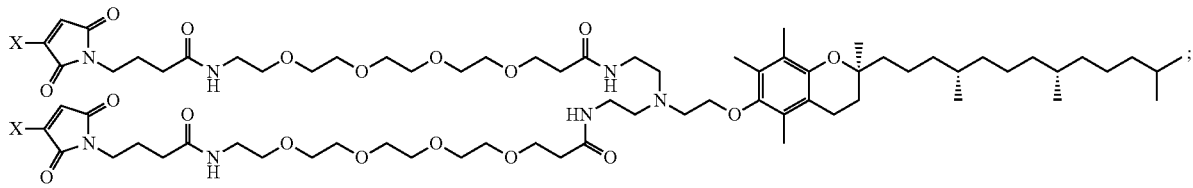

where X is PPISLERLDVGTNLGNAIAKLEDAKEL-LESSDQILR-GSGSG-C(SEQ ID NO: 1).

In some embodiments, the inhibitor of the present invention further comprises an immunogenic carrier molecule linked to the C-terminal peptide or to the tocopherol, tocopherol derivative, or a pharmaceutically acceptable salt thereof. In some cases, the immunogenic carrier molecule may be covalently or non-covalently bound to the peptide. Exemplary immunogenic carrier molecules include, but are not limited to, bovine serum albumin, chicken egg ovalbumin, keyhole limpet hemocyanin, tetanus toxoid, diphtheria toxoid, thyroglobulin, a pneumococcal capsular polysaccharide, CRM 197, and a meningococcal outer membrane protein.

In other embodiments, the inhibitor of the present invention further comprises one or more cell penetrating peptides ("CPP") linked to the C-terminal peptide. CPPs may be derived from, for example, the HIV trans-activator of transcription ("TAT") protein. In one embodiment, the CPP includes the TAT peptide sequence YGRKKRRQRRR (SEQ ID NO: 2). The HIV protein TAT plays an important role in viral pathogenesis. TAT is secreted by HIV infected cells and, having the capacity to cross cell membranes, it is taken up by infected and uninfected cells. In infected cells, its main function is to activate viral transcription. Sequences derived from HIV TAT proteins can be used to improve the localization of peptides into target cells. In another embodiment, the CPP is derived from the C105Y peptide having the sequence PFVYLI (SEQ ID NO: 3). Further CPPs are found in WO 2014/086835 to Strieker et al., which is hereby incorporated by reference in its entirety.

In alternate embodiments, the HRC peptide is derived from Measles virus and the inhibitor is selected from the group consisting of MV HRC5 and MV HRC6. In additional embodiments, the HRC peptide is derived from Human parainfluenza virus and the inhibitor is VIKI-PEG4-tocopherol; the HRC peptide is derived from Nipah virus and the inhibitor is VIKI-PEG4-tocopherol; or the HRC peptide is derived from Ebola virus and the inhibitor is TAT-Ebola-PEG4-toco.

Another aspect of the present invention relates to a pharmaceutical composition including the inhibitor of the present invention and an adjuvant.

In accordance with this aspect of the invention, the composition may further comprise one or more adjuvants. Suitable adjuvants are known in the art and include, without limitation, flagellin, Freund's complete or incomplete adjuvant, aluminum hydroxide, lysolecithin, pluronic polyols, polyanions, peptides, oil emulsion, dinitrophenol, iscomatrix, and liposome polycation DNA particles.

Another aspect of the present invention relates to a method of inhibiting viral fusion in a subject. The method includes selecting a subject infected with or at risk of being infected with a virus and administering to the selected subject the inhibitor or pharmaceutical composition of the present invention under conditions effective to inhibit viral fusion. This aspect is carried out in accordance with the previously described aspects.

Some enveloped viruses, notably paramyxoviruses, retroviruses, and herpesviruses, are capable of fusion with the cell plasma membrane at the cell surface. Binding of the virus to the cell-surface receptor leads to fusion between the virion lipid envelope and the cell plasma membrane. This releases the viral nucleocapsid into the cytoplasm of the host cell, effecting penetration of the host-cell plasma membrane. As described herein, the surface fusion of these enveloped viruses is promoted by virion surface proteins. Other viruses, notably the enveloped Semliki Forest and influenza viruses, enter cells by an endocytotic pathway that exploits a normal cellular pathway for uptake of materials bound to cell-surface receptors. After binding of the viruses to the cell surface, a clathrin-coated invagination of the plasma membrane, called a coated pit, is formed. An endocytotic vesicle then pinches off with the virion particle inside. Acidification of the interior of the vesicle, called an endosome, is then promoted by a proton pump in the membrane. As the pH drops, a virion surface protein(s) undergoes a conformational change, causing exposure of a hydrophobic portion of a virion surface protein. As described herein, this hydrophobic region promotes fusion between the virion lipids envelope and the vesicle membrane, releasing the nucleocapsid into the cytoplasm of the cell. Thus, for enveloped viruses, this mechanism is similar to surface fusion, except that fusion of the viral envelope with the cell membrane occurs within the host cell. As described herein, the inhibitor of the invention is able to inhibit either intracellular or extracellular enveloped virus fusion.

A further aspect of the present invention relates to a method of blocking viral spread in a subject. The method includes selecting a subject infected with or being infected with a virus and administering to the selected subject the inhibitor or pharmaceutical composition of the present invention under conditions effective to block viral spread.

Viral infections spread based on the ability of viruses to overcome multiple barriers and move from cell to cell, tissue to tissue, and person to person and even across species. While there are fundamental differences between these types of transmissions, it has emerged that the ability of viruses to utilize and manipulate cell-cell contact contributes to the success of viral infections. Central to the excitement in the field of virus cell-to-cell transmission is the idea that cell-to-cell spread is more than the sum of the processes of virus release and entry. This implies that virus release and entry are efficiently coordinated to sites of cell-cell contact, resulting in a process that is distinct from its individual components. As described herein, the inhibitor of the invention is able to inhibit virus spread.

Another aspect of the present invention relates to a method of preventing or treating a viral infection resulting from an enveloped virus in a subject. This method includes selecting a subject infected with or at risk of being infected with a virus and administering to the selected subject the inhibitor or pharmaceutical composition of the present invention under conditions effective to prevent or treat a viral infection resulting from an enveloped virus.

In carrying out the methods of the present invention, the inhibitor is configured substantially as described above.

In accordance with these aspects of the present invention, infections resulting from an enveloped virus include, without limitation, any virus resulting from an infection by an enveloped virus such as Togaviridae, Flaviviridae, Coronaviridae, Rhabdoviridae, Filoviridae, Paramyxoviridae, Orthomyxoviridae, Bunyaviridae, Arenaviridae, Retroviridae, Herpesviridae, Poxviridae and Iridoviridae.

For purposes of these aspects of the present invention, the target "subject" encompasses any animal, preferably a mammal, more preferably a human. In the context of inhibiting viral fusion, blocking viral spread, and administering a composition of the invention for purposes of preventing an infection resulting from an enveloped virus in a subject, the target subject encompasses any subject that is at risk of being infected by an infection resulting from an enveloped virus. Particularly susceptible subjects include infants and juveniles, as well as immunocompromised juvenile, adults, and elderly adults. However, any infant, juvenile, adult, or elderly adult or immunocompromised individual at risk for infections resulting from an enveloped virus can be treated in accordance with the methods of the present invention. In the context of inhibiting viral fusion, blocking viral spread, and administering a composition of the invention for purposes of treating an infection resulting from an enveloped virus infection in a subject, the target subject population encompasses any subject infected with an infection resulting from an enveloped virus. Particularly suitable subjects include those at risk of infection or those infected with a virus selected from the group consisting of Measles virus, Ebola virus, Human parainfluenza virus, Nipah virus, and HIV-1. In one embodiment, the subject is infected with Measles virus and the inhibitor is selected from the group consisting of MV HRC5 and MV HRC6. In another embodiment, the subject is infected with Human parainfluenza virus and the inhibitor is VIKI-PEG4-tocopherol. In yet another embodiment, the subject is infected with Nipah virus and the inhibitor is VIKI-PEG4-tocopherol. In yet another embodiment, the subject is infected with Ebola virus and the inhibitor is TAT-Ebola-PEG4-toco.

In the context of inhibiting viral fusion, blocking viral spread, and using the therapeutic compositions of the present invention to prevent an infection resulting from an enveloped virus infection, the concentration of inhibitor of fusion between a viral membrane and a cell membrane in the composition are adequate to achieve the prevention of infection resulting from an enveloped virus infection, particularly the prevention of infection resulting from an enveloped virus infection in susceptible populations. In the context of using therapeutic compositions to treat an infection resulting from an enveloped virus, the amount administered is capable of achieving a reduction in a number of symptoms, a decrease in the severity of at least one symptom, or a delay in the further progression of at least one symptom, or even a total alleviation of the infection.

Therapeutically effective amounts of inhibitor of fusion between a viral membrane and a cell membrane can be determined in accordance with standard procedures, which take numerous factors into account, including, for example, the concentrations of these active agents in the composition, the mode and frequency of administration, the severity of the infection to be treated (or prevented), and subject details, such as age, weight and overall health and immune condition. General guidance can be found, for example, in the publications of the International Conference on Harmonization and in REMINGTON'S PHARMACEUTICAL SCIENCES (Mack Publishing Company 1990), which is hereby incorporated by reference in its entirety. A clinician may administer the inhibitor of the present invention, until a dosage is reached that provides the desired or required prophylactic or therapeutic effect. The progress of this therapy can be easily monitored by conventional assays.

Therapeutically effective amounts of the inhibitor of fusion between a viral membrane and a cell membrane will depend on whether adjuvant is co-administered, with higher dosages being required in the absence of adjuvant. The amount of inhibitors for administration sometimes varies from 1 µg-500 µg per patient and more usually from 5-500 µg per for human administration. The timing of administrations can vary significantly from once a day, to once a year, to once a decade, to once a lifetime. Generally an effective dosage can be monitored by obtaining a fluid sample from the subject, generally a blood serum sample, using methods well known in the art and readily adaptable to the specific virus to be measured. Ideally, a sample is taken prior to initial dosing and subsequent samples are taken and titered after each administration. Generally, a dose or dosing schedule which provides a detectable titer at least four times greater than control or "background" levels at a serum dilution of 1:100 is desirable, where background is defined relative to a control serum or relative to a plate background in ELISA assays.

Therapeutically effective amount of the inhibitor of the present invention typically occurs in doses ranging from 0.1 mg composition per kilogram of body weight (mg/kg) up to 1000 mg/kg, including at least 100 mg/kg, at least 150 mg/kg, at least 200 mg/kg, at least 250 mg/kg, at least 500 mg/kg, at least 750 mg/kg, and at least 1000 mg/kg, per dose or on a daily basis. The dosage may alternatively be lower, such as 0.3, 1.0, 3, 5, 7.5, or at least about 5 mg/kg, at least about 10 mg/kg, at least about 15 mg/kg, at least about 20 mg/kg, or at least about 25 mg/kg. An amount effective to treat the disorders herein before described depends upon such factors as the efficacy of the active compounds, the molecular weight of the agent chosen, the nature and severity of the disorders being treated and the weight of the mammal. However, a unit dose will normally contain 0.01 to 200 mg, for example 5 to 100 mg, of the compound of the invention. "Unit dose" includes a discrete amount of the pharmaceutical composition comprising a predetermined amount of the active ingredient. In certain embodiments, the administering is repeated. Intervals between single dosages can be weekly, monthly or yearly. Intervals can also be irregular as indicated by measuring blood levels of inhibitor in the subject. Alternatively, inhibitor can be administered as a sustained release formulation, in which case less frequent administration is required. The dosage and frequency of administration can vary depending on whether the treatment is prophylactic or therapeutic. In prophylactic applications, a relatively low dosage is administered at relatively infrequent intervals over a long period of time. In therapeutic applications, a relatively high dosage at relatively short intervals is sometimes required until progression of the virus is reduced or terminated, and preferably until the subject shows partial or complete amelioration of symptoms of virus.

Pharmaceutical compositions of the present invention may be administered in a single dose, or in accordance with a multi-dosing protocol. For example, relatively few doses of the therapeutic composition are administered, such as one or two doses. However, the different dosages, timing of dosages and relative amounts of the therapeutic composition can be selected and adjusted by one of ordinary skill in the art.

Pharmaceutical compositions for of the present invention can be administered orally, by inhalation, by intranasal instillation, topically, transdermally, intraplurally, intraperitoneally, by application to a mucous membrane, parenterally, topically, intravenously, orally, subcutaneously, intraperitoneally, intranasally or by intramuscular means for prophylactic and/or therapeutic treatment. The most typical route of administration is by application of mucous membrane although subcutaneous and others can be equally effective. Intramuscular injection is also useful as a route of administration. This type of injection is most typically performed in the arm or leg muscles. Intravenous injections as well as intraperitoneal injections, intra-arterial, intracranial, or intradermal injections are also effective in generating an immune response.

The pharmaceutical compositions of the present invention may be formulated for parenteral administration. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Compositions suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the compositions of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices such as those described by Medtronic, Northridge, Calif. Such devices allow continuous infusion of desired compounds avoiding multiple injections and multiple manipulations.

EXAMPLES

The examples below are intended to exemplify the practice of embodiments of the disclosure but are by no means intended to limit the scope thereof.

Materials and Methods for Examples 1-5

Plasmids and Reagents:
The genes of MV G954 wt H and wt F were codon optimized, synthesized and subcloned into the mammalian expression vector pCAGGS.

Peptide Synthesis:
All peptides were produced by standard Fmoc-solid phase methods. The cholesterol or tocopherol moieties were attached to the peptides via chemoselective reaction between the thiol group of an extra cysteine residue, added C-terminally to the sequence, and a bromoacetyl derivative of cholesterol or tocopherol or a bis-maleimide functionalized cholesterol or tocopherol core, as previously described for cholesterol (Porotto et al., "Inhibition of Nipah Virus Infection In Vivo: Targeting an Early Stage of Paramyxovirus Fusion Activation during Viral Entry," *PLoS Pathog.* 6(10) e1001168 (2010); Ingallinella et al., "Addition of a Cholesterol Group to an HIV-1 Peptide Fusion Inhibitor Dramatically Increases its Antiviral Potency," *Proc. Natl. Acad. Sci. U.S.A.* 106:5801-6 (2009); and Pessi et al., "A General Strategy to Endow Natural Fusion-Protein-Derived Peptides with Potent Antiviral Activity," *PLoS One* 7:e36833 (2012), which are hereby incorporated by reference in their entirety).

Transient Expression of H and F Genes:
Transfections were performed in 293T cells according to the Lipofectamine 2000 manufacturer's protocols (Invitrogen).

Cells and Viruses:
293T (human kidney epithelial cells) and Vero-SLAM (African green monkey kidney cells) were grown in Dulbecco's modified Eagle's medium (DMEM) (GIBCO; Invitrogen) supplemented with 10% fetal bovine serum and antibiotics in 5% CO2. The Vero-SLAM culture medium was supplemented with geneticin. Wild type MV strain G954 (genotype B3.2) were isolated in Gambia in 1993 (Kouomou et al., "Adaptation of Wild-Type Measles Virus to Tissue Culture," *J. Virol.* 76:1505-9 (2002), which is hereby incorporated by reference in its entirety). Recombinant MV IC323, expressing EGFP (MV-IC323-EGFP) (Hashimoto et al., "SLAM (CD150)-Independent Measles Virus Entry as Revealed by Recombinant Virus Expressing Green Fluorescent Protein," *J. Virol.* 76:6743-9 (2002), which is hereby incorporated by reference in its entirety). Both virus strains were propagated and titrated on Vero SLAM cells.

Viral Entry Assay:

Vero-SLAM monolayer cells were incubated with 40-50 PFU of wild type MV G954 in the presence of various concentrations of peptides. After 90 minutes, 2× minimal essential medium containing 10% FBS was mixed with 1% avicell and added to the dishes. The plates were then incubated at 37° C. for 72 h. After removing the medium overlay, the cells were immunostained for plaque detection. The number of plaques in the control (no peptide) and experimental wells were counted under a dissecting stereoscope.

Viral Spread Assay:

Vero-SLAM monolayer cells were incubated with 25 PFU of wild type MV-IC323-EGFP. After 120 min, the virus was taken off and medium with various concentrations of peptides was added. After 72 h, fluorescence was read with the spectramax M5 plate reader (Porotto et al., "Simulating Henipavirus Multicycle Replication in a Screening Assay Leads to Identification of a Promising Candidate for Therapy," *J. Virol.* 83:5148-5155 (2009), which is hereby incorporated by reference in its entirety).

Beta-Galactosidase Complementation-Based Fusion Assay:

This fusion assay (Moosmann et al., "Alpha Complementation of LacZ in Mammalian Cells," *Nuc. Acids Res.* 24:1171-2 (1996), which is hereby incorporated by reference in its entirety) is based on alpha complementation of beta-gal; the beta-gal protein lacking the N-terminal 85 residues (omega peptide) is expressed from one plasmid, and the N-terminal 85 residues (alpha peptide) is expressed from a second plasmid. Cell fusion leads to complementation, and beta-galactosidase is quantitated using the Galacto-Star (Applied Biosystems) chemiluminescent reporter gene assay system. 293T Cells transiently transfected with SLAM and the omega peptide were incubated with cells co-expressing viral glycoproteins (MV H and MV F) that also express the alpha peptide. Fusion was measured after 6 hours by lysing the cells with lysis buffer and adding the substrate (Porotto et al., "Inhibition of Nipah Virus Infection In Vivo: Targeting an Early Stage of Paramyxovirus Fusion Activation during Viral Entry," *PLoS Pathog.* 6(10)e1001168 (2010), which is hereby incorporated by reference in its entirety).

Infection of Mice:

SLAM×IFNAR KO transgenic ("tg") mice (Sellin et al., "Current Animal Models: Transgenic Animal Models for the Study of Measles Pathogenesis," *Curr. Top Microbiol. Immunol.* 330:111-27 (2009), which is hereby incorporated by reference in its entirety) were bred at the institute's animal facility (PBES, ENS-Lyon) and used as heterozygotes for SLAM transgene. 3 week old mice were infected intranasally (i.n.) by application of 10 µl of MV G954 in both nares (10000 PFU of MV/mouse). To evaluate the prophylactic effect of HRC peptides, the SLAM×IFNARKO mice were treated with a single intranasal administration of peptides 6 mg/kg 24 hours before the infection. The control mice received the same number of administrations using the diluent. All animals were observed daily for clinical signs (neurological symptoms, ataxia, lethargy) and euthanized once clinical signs were observed. Protocol was approved by the Regional Ethical Committee (CECCAPP protocol N° ENS-2011-003).

Statistical Analysis:

Data were expressed as mean and standard deviation ("SD"). Statistical analyses were performed using unpaired t test and Mantel cox test and GraphPad Prism software.

Example 1—Design of Measles Virus Peptide Fusion Inhibitors

The antiviral activity of peptides derived from the HRC region of the fusion protein differs considerably among enveloped viruses (Harrison, "Viral Membrane Fusion," *Nat. Struct. Mol. Biol.* 15:690-8 (2008); Pessi et al., "A General Strategy to Endow Natural Fusion-Protein-Derived Peptides with Potent Antiviral Activity," *PLoS One* 7:e36833 (2012); Vigant et al., "Hendra and Nipah Infection: Pathology, Models and Potential Therapies," *Infect. Dis. Drug Targets* 11:315-36 (2011); and Eckert et al., "Mechanisms of Viral Membrane Fusion and its Inhibition," *Ann. Rev. Biochem.* 70:777-810 (2001), which are hereby incorporated by reference in their entirety). The potency, especially for weak inhibitors, can be increased by peptide engineering strategies. Based on previous experience with optimizing antiviral properties of HRC-specific peptides (Porotto et al., "Inhibition of Nipah Virus Infection In Vivo: Targeting an Early Stage of Paramyxovirus Fusion Activation during Viral Entry," *PLoS Pathog.* 6(10)e1001168 (2010) and Pessi et al., "A General Strategy to Endow Natural Fusion-Protein-Derived Peptides with Potent Antiviral Activity," *PLoS One* 7:e36833 (2012), which are hereby incorporated by reference in their entirety), lipid-conjugation and dimerization strategies were applied to the design of MV F derived fusion inhibitors. The amino acid sequence and the modifications introduced in the peptides used in this study are shown in FIG. 1A.

The peptide sequence was derived from the HRC region (residues 450-485) of MV F, and extended with a C-terminal GSGSG linker/spacer sequence and a cysteine residue, which allowed for conjugation to cholesterol via thiol-reactive reagents. This core amino acid sequence was used for the subsequent modifications. The control peptide sequence (MV HRC1) featured the cysteine residue alkylated with iodoacetamide. Similar to the previously reported NiV, HPIV3 and HIV inhibitors (Pessi et al., "A General Strategy to Endow Natural Fusion-Protein-Derived Peptides with Potent Antiviral Activity," *PLoS One* 7:e36833 (2012), which is hereby incorporated by reference in its entirety), reaction of the core sequence with a bromoacetyl derivative of cholesterol featuring a 4-unit polyethyleneglycol spacer ("PEG4") produced the cholesterol-conjugated monomer (MV HRC2), while reaction with a bis-maleimide-functionalized PEG4 with and without the cholesterol moiety produced the HRC dimer (MV HRC3) and the cholesterol-conjugated dimer (MV HRC4). The same reaction was used to prepare the corresponding monomer (MV HRC5) and dimer (MV HRC6) conjugated with tocopherol.

Example 2—Inhibition of Wild-Type MV Entry by MV F Derived Peptides

Figure 2A:
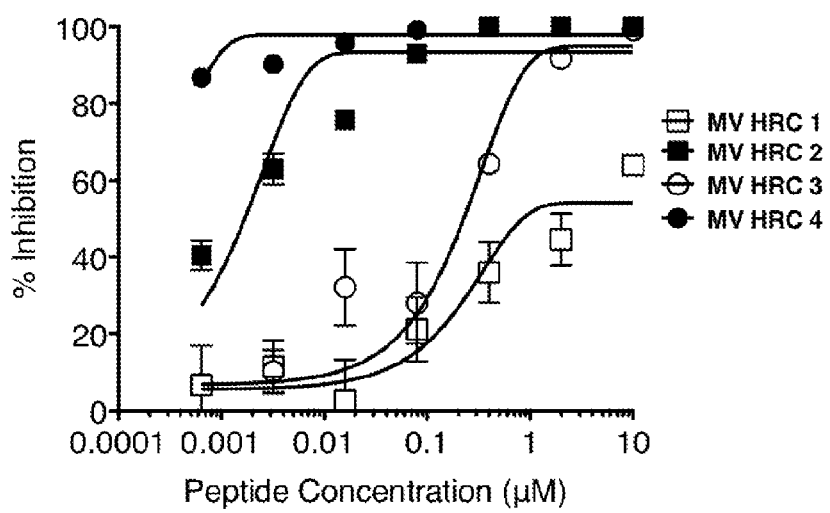
FIGS. 2A-2B illustrate the interactions of MV HRC peptides with MV.

The inhibitory activities of MV HRC 1, MV HRC 2, MV HRC 3 and MV HRC 4 (FIG. 1) against wt MV G954 were assessed in plaque reduction assays (FIG. 2A). Both peptides containing the cholesterol moiety (MV HRC2 and HRC4) performed better than their unconjugated counterparts (MV HRC1 and HRC3). While for the unconjugated peptides the $IC_{50}$ values were ~7000 nM (MV HRC 1) and ~300 nM (MV HRC3), for the cholesterol-conjugated peptides the $IC_{50}$ values were only ~2 nM (MV HRC2) and ~0.5 nM (MV HRC4). The dimeric peptide with cholesterol outperformed the other peptides over a wide range of concentrations. The data in FIG. 2A indicate that dimerization and cholesterol conjugation independently improve the overall efficacy of the entry inhibitor against MV, and that the effects of cholesterol and of dimerization are additive. Similar results were obtained with the MV-IC323-EGFP wt strain.

Example 3—Spread of Virus is Curtailed by the Dimeric Lipid-Conjugated Peptides

Figure 2B:
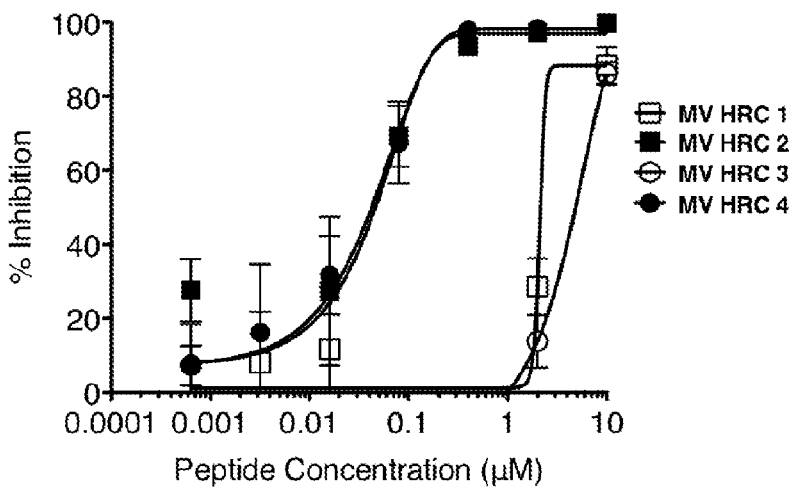

For clinical utility, the ability of an antiviral agent to prevent multiple rounds of infection is key (Talekar et al., "Infection of Primary Neurons Mediated by Nipah Virus Envelope Proteins: Role of Host Target Cells in Antiviral Action," *J. Virol.* 85:8422-6 (2011), which is hereby incorporated by reference in its entirety). A multicycle replication assay (Porotto et al., "Simulating Henipavirus Multicycle Replication in a Screening Assay Leads to Identification of a Promising Candidate for Therapy," *J. Virol.* 83:5148-5155 (2009), which is hereby incorporated by reference in its entirety) was adapted to assess the effect of the cholesterol-conjugated peptides on viral infection in Vero SLAM cells after infection, with the use of a MV wt virus carrying the EGFP gene, MV-IC323-EGFP (Hashimoto et al., "Measles Virus Entry as Examined by a Recombinant Virus Expressing Green Fluorescent Protein," *Uirusu.* 52:169-75 (2002), which is hereby incorporated by reference in its entirety). A Vero-SLAM monolayer was infected with MV-IC323-EGFP virus and after a 120-minute adsorption period to permit viral entry, the medium was replaced with fresh medium containing different concentrations of peptides as indicated on the x-axis in FIG. 2B. The fluorescence level, which reflects the amount of infection by the EGFP-encoding virus in the Vero SLAM cells, was quantitated after 72 hours as previously described (Porotto et al., "Simulating Henipavirus Multicycle Replication in a Screening Assay Leads to Identification of a Promising Candidate for Therapy," *J. Virol.* 83:5148-5155 (2009), which is hereby incorporated by reference in its entirety). Under these conditions, when viral entry had already occurred, only the cholesterol-conjugated peptides exhibited antiviral activity. The unconjugated peptides did not prevent viral spread. FIG. 2B shows that at three days post-infection, neither MV HRC 1 nor MV HRC 3 reduced viral infection; the fluorescence level in the presence of these peptides was the same as for untreated control wells. At the same time point, the $IC_{50}$ for MV HRC 2 peptide was ~54 nM, similar to that for the MV HRC 4 dimeric peptide (~55 nM under the same conditions), indicating that the cholesterol-conjugated peptides prevent the spread of the virus.

Example 4—Cell-to-Cell Fusion is Inhibited by MV F Derived Peptides

Figures 3, 4:
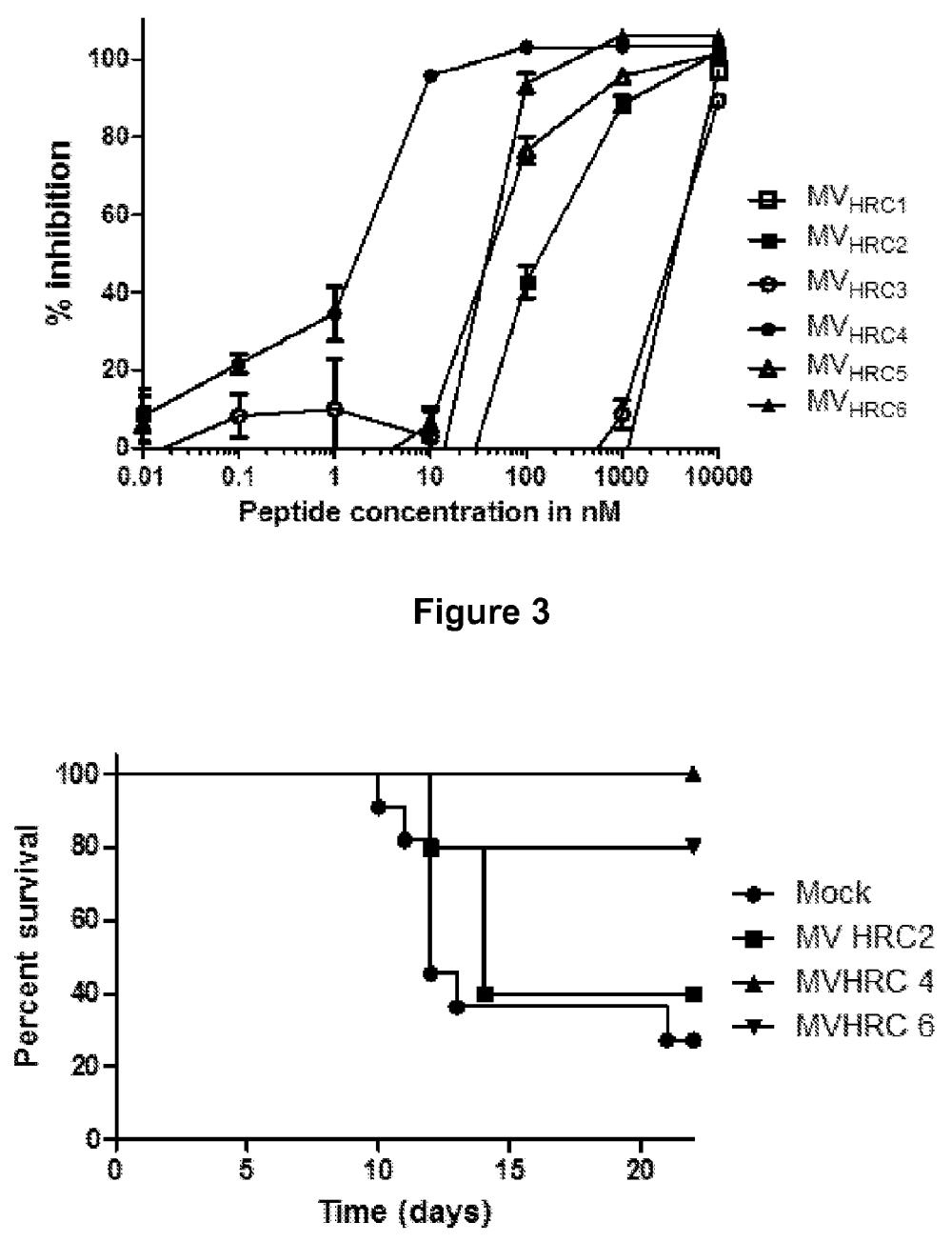

While the two unconjugated peptides completely lost their inhibitory efficacy at 1000 nM in the assay for viral spread as described above (FIG. 2B), they retained their inhibitory capacity in the simple viral entry assay at this concentration (FIG. 2A). The cholesterol-conjugated peptides inhibited infection in both assays at 1000 nM. To investigate the reason for this difference, a quantitative fusion assay was performed based on beta-galactosidase ("beta-gal") complementation, in which expression of beta-gal results from the fusion of cells expressing viral envelope glycoproteins (i.e., MV G954 H/F) with cells expressing the MV receptor SLAM. To better understand whether another lipid could show similar properties, the corresponding monomer and dimer conjugated with tocopherol, respectively called MV HRC5 and MV HRC6, were tested in parallel. The indicated concentrations of MV HRC peptides were present during the entire fusion process, thus allowing peptides to act at the stages of triggering/activation of the fusion protein as well as during subsequent fusion. The cells were lysed after 6 hours of incubation and the fusion was quantitated by measuring beta-gal complementation (FIG. 3). The results obtained showed not only that cholesterol-conjugation highly improved the fusion inhibition properties of the monomer (MV HRC2), but also that monomer fusion inhibitor with tocopherol-conjugation performed even better inhibition (MV HRC5). The dimeric peptide with cholesterol (MV HRC4) showed the greatest anti-viral potential in terms of $IC_{50}$, while the corresponding peptide with tocopherol-conjugation (MV HRC6) showed a significantly improved $IC_{50}$ relative to that obtained with the monomer.

Example 5—Inhibition of MV Infection In Vivo by the Lipid-Conjugated Dimer Peptide Several cell surface receptors have been shown to interact with MV: CD46 in laboratory MV strains, CD150 (or SLAM) in both wild-type and laboratory MV strains, and finally nectin-4, recently found to promote viral egress from the respiratory tract (Muhlebach et al., "Adherens Junction Protein Nectin-4 is the Epithelial Receptor for Measles Virus," *Nature* 2011 and Noyce et al., "Tumor Cell Marker PVRL4 (Nectin 4) is an Epithelial Cell Receptor for Measles Virus," *PLoS Pathog.* 7:e1002240 (2011), which are hereby incorporated by reference in their entirety). It is not yet known how MV enters the brain; it has been suggested that for development of MV-induced CNS manifestations specific MV H receptors may not be necessary, as the virus seems to spread without budding, implicating direct cell-to-cell and trans-synaptic transmission (Ehrengruber et al., "Measles Virus Spreads in Rat Hippocampal Neurons by Cell-To-Cell Contact and in a Polarized Fashion," *J. Virol.* 76:5720-8 (2002); Makhortova et al., "Neurokinin-1 Enables Measles Virus Trans-Synaptic Spread in Neurons," *Virology* 362:235-44 (2007); and Lin et al., "Prolonged Persistence of Measles Virus RNA is Characteristic of Primary Infection Dynamics," *Proc. Nat. Acad. Sci. U.S.A.* 109:14989-94 (2012), which are hereby incorporated by reference in their entirety). The presence of F protein, and alterations in its fusion phenotype, have been associated with severe CNS infections (Lawrence et al., "Measles Virus Spread Between Neurons Requires Cell Contact but not CD46 Expression, Syncytium Formation, or Extracellular Virus Production," *J. Virol.* 74:1908-18 (2000), which is hereby incorporated by reference in its entirety); if F-mediated membrane fusion is blocked, viral spread between neurons is halted (Makhortova et al., "Neurokinin-1 Enables Measles Virus Trans-Synaptic Spread in Neurons," *Virology* 362:235-44 (2007) and Watanabe et al., "Mutant Fusion Proteins with Enhanced Fusion Activity Promote Measles Virus Spread in Human Neuronal Cells and Brains of Suckling Hamsters," *J. Virol.* 2012, which are hereby incorporated by reference in their entirety). These findings suggest that it may be possible to halt CNS infection by targeting the F protein and its function.

It has previously been shown that intranasal infection with wild-type MV of either suckling CD150 mice or adult CD150 mice that are crossed in an interferon receptor deficient background (i.e., the SLAM×IFNARKO) led to development of an acute neurological syndrome characterized by lethargy, seizures, ataxia, weight loss, and death (Sellin et al., "Current Animal Models: Transgenic Animal Models for the Study of Measles Pathogenesis," *Curr. Top Microbiol. Immunol.* 330:111-27 (2009) and Sellin et al., "High Pathogenicity of Wild-Type Measles Virus Infection in CD150 (SLAM) Transgenic Mice," *J. Virol.* 80:6420-9 (2006), which are hereby incorporated by reference in their entirety). This model, in allowing a simple readout of the efficacy of an anti-viral treatment, provides an accurate experimental means to test novel anti-MV preventive and therapeutic strategies (Sellin et al., "High Pathogenicity of Wild-Type Measles Virus Infection in CD150 (SLAM) Transgenic Mice," *J. Virol.* 80:6420-9 (2006) and Sellin et al., "Interplay Between Virus-Specific Effector Response and Foxp3 Regulatory T Cells in Measles Virus Immunopathogenesis," *PLoS One* 4:e4948 (2009), which are hereby incorporated by reference in their entirety). This study was designed to establish proof of concept for the utilization of HRC peptides in the prevention and treatment of measles neurological complications both in non-vaccinated or immunodepressed people.

The SLAM×IFNARKO adult mouse model was used to analyze whether cholesterol coupled MV-HRC peptides provide protection from fatal measles encephalitis (FIG. 4). Initial experiments demonstrated the absence of any toxicity in mice after one-week treatment with 6 mg/kg of the MV-HRC peptides. Interestingly, while a single intranasal administration of MV HRC2 24 hours before infection did not really improve the animal survival, almost all mice where protected (80% to 100%) when pre-treated with the dimeric form of the peptide either conjugated with cholesterol or with tocopherol.

Discussion of Examples 1-5

MV infection causes an acute respiratory illness whose symptoms include fever and rash, and may be associated with a profound suppression of the immune system that permits opportunistic infections. In addition, neurological sequelae of measles can affect individuals within days to years after acute measles infection, often resulting in severe disability and death (Hosoya, "Measles Encephalitis: Direct Viral Invasion or Autoimmune-Mediated Inflammation?" *Internal Med.* 45:841-2 (2006) and Buchanan et al., "Measles Virus and Associated Central Nervous System Sequelae," *Seminars Ped. Neurol.* 19:107-14 (2012), which are hereby incorporated by reference in their entirety). While acute post-infectious encephalomyelitis occurs during or shortly after acute measles primarily in older children and adults, SSPE presents a late neurodegenerative complication of measles, with an incubation period of several years, and is associated with persistent infection of brain cells (Allen et al., "The Significance of Measles Virus Antigen and Genome Distribution in the CNS in SSPE for Mechanisms of Viral Spread and Demyelination," *J. Neuropathol. Exper. Neurol.* 55:471-80 (1996), which is hereby incorporated by reference in its entirety).

Measles is a reemerging disease. Although high vaccination coverage has significantly reduced the incidence of measles, outbreaks are still occurring all around the world, with resurgence in industrialized countries during last few years. There were approximately 42,000 laboratory confirmed measles cases worldwide in 2012.

Although vaccination remains the most effective method for controlling measles, therapy is essential because various issues prevent the 95% vaccination coverage that would be necessary for worldwide measles elimination. In addition, immunocompromised individuals often cannot benefit from vaccination, and represent a particularly vulnerable population (Moss et al., "Measles," *Lancet* 379:153-64 (2012) and Bitnun et al., "Measles Inclusion-Body Encephalitis Caused by the Vaccine Strain of Measles Virus," *Clin. Infect. Dis.* 29:855-61 (1999), which are hereby incorporated by reference in their entirety).

Complications of MV infection occur in up to 40% of cases, and those involving the CNS are rare but serious. Primary measles encephalitis occurs in 1-3 of 1000 infected patients, with recovery of infectious virus from the cerebrospinal fluid or brain (Hosoya, "Measles Encephalitis: Direct Viral Invasion or Autoimmune-Mediated Inflammation?" *Internal Med.* 45:841-2 (2006) and Buchanan et al., "Measles Virus and Associated Central Nervous System Sequelae," *Seminars Ped. Neurol.* 19:107-14 (2012), which are hereby incorporated by reference in their entirety). Another CNS complication, acute postinfectious encephalomyelitis, also occurs during or shortly after acute measles but seems to be associated with an autoimmune etiology, and virus is not isolated. SSPE occurs in 4-11 of 100,000 cases of acute measles, causing progressive dementia, seizures, and ataxia (Allen et al., "The Significance of Measles Virus Antigen and Genome Distribution in the CNS in SSPE for Mechanisms of Viral Spread and Demyelination," *J. Neuropathol. Exper. Neurol.* 55:471-80 (1996), which is hereby incorporated by reference in its entirety). Another form of progressive MV-induced CNS disease, known as measles inclusion body encephalitis ("MIBE"), occurs in immunosuppressed patients 1 to 6 months following measles infection, and is characterized by seizures, motor and sensory deficits, and lethargy, with either an acute or a subacute fatal course. Nonrestricted virus replication, due to an absent or decreased immune response, results in cytolytic viral replication in the brain tissue (Buchanan et al., "Measles Virus and Associated Central Nervous System Sequelae," *Seminars Ped. Neurol.* 19:107-14 (2012); Urbanska et al., "Spread of Measles Virus Through Axonal Pathways into Limbic Structures in the Brain of TAP1−/− Mice," *J. Med. Virol.* 52:362-9 (1997); and Norrby et al., "Measles Virus in the Brain," *Brain Res. Bulletin* 44:213-20 (1997), which are hereby incorporated by reference in their entirety).

There are no specific therapies for these complications of CNS infection, often with lethal outcomes (Makhortova et al., "Neurokinin-1 Enables Measles Virus Trans-Synaptic Spread in Neurons," *Virology* 362:235-44 (2007); O'Donnell et al., "Blue Moon Neurovirology: The Merits of Studying Rare CNS Diseases of Viral Origin," *J. Neuroimmune Pharmacol.* 2010; Young et al., "Making it to the Synapse: Measles Virus Spread in and Among Neurons," *Curr. Top Microbiol. Immunol.* 330:3-30 (2009); and Reuter et al., "Measles Virus Infection of the CNS: Human Disease, Animal Models, and Approaches to Therapy," *Med. Microbiol. Immunol.* 2010, which are hereby incorporated by reference in their entirety). Although treatment of SSPE has been attempted with a broad spectrum of anti-viral drugs, including ribavirin, interferons, and isoprinosin, complete remission has not been achieved (Moss et al., "Measles," *Lancet* 379:153-64 (2012); Plemper et al., "Measles Control—Can Measles Virus Inhibitors Make a Difference?" *Curr. Opin. Invest. Drugs* 10:811-20 (2009); Makhortova et al., "Neurokinin-1 Enables Measles Virus Trans-Synaptic Spread in Neurons," *Virology* 362:235-44 (2007); Lin et al., "Prolonged Persistence of Measles Virus RNA is Characteristic of Primary Infection Dynamics," *Proc. Nat. Acad.*

Sci. U.S.A. 109:14989-94 (2012); O'Donnell et al., "Blue Moon Neurovirology: The Merits of Studying Rare CNS Diseases of Viral Origin," *J. Neuroimmune Pharmacol.* 2010; Young et al., "Making it to the Synapse: Measles Virus Spread in and Among Neurons," *Curr. Top Microbiol. Immunol.* 330:3-30 (2009); Reuter et al., "Measles Virus Infection of the CNS: Human Disease, Animal Models, and Approaches to Therapy," *Med. Microbiol. Immunol.* 2010; and Griffin et al., "Measles Virus, Immune Control, and Persistence," *FEMS Microbiol. Rev.* 36:649-62 (2012), which are hereby incorporated by reference in their entirety). Therefore, in addition to vaccination, establishment of effective prophylactic therapies for MV CNS infection is important. Examples 1-5 provide evidence that MV HRC derived peptides have the potential to fill this void.

The data presented in Examples 1-5 above support earlier data demonstrating that dimerization and cholesterol conjugation increase the inhibitory activity of other viral fusion inhibitory peptides (Porotto et al., "Inhibition of Nipah Virus Infection In Vivo: Targeting an Early Stage of Paramyxovirus Fusion Activation during Viral Entry," *PLoS Pathog.* 6(10)e1001168 (2010) and Pessi et al., "A General Strategy to Endow Natural Fusion-Protein-Derived Peptides with Potent Antiviral Activity," *PLoS One* 7:e36833 (2012), which are hereby incorporated by reference in their entirety). Peptides derived from the HRC region of measles virus F have been known to inhibit the virus (Wild et al., "Inhibition of Measles Virus Infection and Fusion with Peptides Corresponding to the Leucine Zipper Region of the Fusion Protein," *J. Gen. Virol.* 78 (Pt 1):107-11 (1997), which is hereby incorporated by reference in its entirety). These results show that the efficacy of these peptides increased with dimerization and with cholesterol- or tocopherol-conjugation against cell fusion after prolonged exposure to cells in culture. The dimerized lipid conjugated peptides were also efficacious in vivo. These results in combination with previous studies using Nipah virus inhibitors (Porotto et al., "Inhibition of Nipah Virus Infection In Vivo: Targeting an Early Stage of Paramyxovirus Fusion Activation during Viral Entry," *PLoS Pathog.* 6(10)e1001168 (2010) and Pessi et al., "A General Strategy to Endow Natural Fusion-Protein-Derived Peptides with Potent Antiviral Activity," *PLoS One* 7:e36833 (2012), which are hereby incorporated by reference in their entirety) point to the fusion inhibitory efficacy as a predictive tool of in vivo efficacy. Future studies will investigate the development of more effective fusion inhibitors, with the underlying hypothesis that such inhibitors will perform better in vivo.

Example 5 above shows that a single intranasal administration of the dimeric lipid conjugated peptide protected 80 to 100% of the mice from MV infection, making the peptide a strong candidate for prophylactic therapy. The data presented above show that an F targeting inhibitor can block MV infection.

Although previous studies have shown the ability of an anti-fusion tripeptide, FIP, to inhibit infection by vaccine virus, and to prevent the fusion by a neuropathogenic MV strain in vitro at very high concentrations (200 µM), the tripeptide was not shown to have in vivo activity (Francis et al., "Design of a Modular Tetrameric Scaffold for the Synthesis of Membrane-Localized d-Peptide Inhibitors of HIV-1 Entry," *Bioconjugate Chem.* (2012), which is hereby incorporated by reference in its entirety). Furthermore, the HIV fusion-inhibitory peptide enfuvirtide, which targets the HIV gp41 HRC, is presently used as a salvage therapy for multidrug-resistant HIV-1-infected patients but its negligible distribution in the CNS—typical of peptide and antibody drugs—precludes its use for HIV-1 dementia and encephalitis. Thus, the brain-penetrating capacity of lipid-conjugated peptides, previously described (Porotto et al., "Inhibition of Nipah Virus Infection In Vivo: Targeting an Early Stage of Paramyxovirus Fusion Activation during Viral Entry," *PLOS Pathog.* 6(10): e1001168 (2010), which is hereby incorporated by reference in its entirety), is a key feature that supports their further development as CNS therapeutics when way of administrations are combined.

Having obtained proof of concept for using lipid-conjugated fusion inhibitors to prevent MV infection of the brain, several options can be explored to improve their efficacy. For example, optimizing the length of the linker joining the monomers may increase the potency (Francis et al., "Design of a Modular Tetrameric Scaffold for the Synthesis of Membrane-Localized d-Peptide Inhibitors of HIV-1 Entry," *Bioconjugate Chem.* 23(6): 1252-8 (2012), which is hereby incorporated by reference in its entirety), consistent with the finding that the 4-unit polyethylenglycol (PEG4) spacer used herein greatly enhanced the activity of NiV and HPIV3 inhibitors (Porotto et al., "Inhibition of Nipah Virus Infection In Vivo: Targeting an Early Stage of Paramyxovirus Fusion Activation during Viral Entry," *PLOS Pathog.* 6(10): e1001168 (2010), which is hereby incorporated by reference in its entirety). Then, the use of tocopherol conjugation instead of cholesterol may improve the peptide efficacy against other viruses more susceptible to the already well known antiviral properties of this antioxidant/vitamin. Likewise, optimization of the interhelical packing interactions of the HRC peptide with the cognate HRN region of F should be beneficial, as previously noted (Porotto et al., "Inhibition of Nipah Virus Infection In Vivo: Targeting an Early Stage of Paramyxovirus Fusion Activation during Viral Entry," *PLOS Pathog.* 6(10): e1001168 (2010), which is hereby incorporated by reference in its entirety). Furthermore, since it has been suggested that MV spread within the CNS requires the F glycoprotein (Young et al., "Making it to the Synapse: Measles Virus Spread in and Among Neurons," *Curr. Top Microbiol. Immunol.* 330: 3-30 (2009), which is hereby incorporated by reference in its entirety), peptides designed to completely block the F protein may be better for treatment of CNS complications. Finally, as some SSPE strains have mutations in the F protein that cause enhanced fusion activity (Watanabe et al., "Mutant Fusion Proteins with Enhanced Fusion Activity Promote Measles Virus Spread in Human Neuronal Cells and Brains of Suckling Hamsters," *J. Virol.* 87(5): 2649-59 (2013), which is hereby incorporated by reference in its entirety), the efficacy of HRC peptides vs. those strains remains to be determined.

Already at this stage, the peptides may provide a combined MV prophylaxis and therapy for protecting immunocompromised individuals, infants prior to vaccination, patients who decline vaccination, and for rapid control of local outbreaks (Moss et al., "Measles," *Lancet* 379:153-64 (2012), which is hereby incorporated by reference in its entirety). Finally, the efficacy of peptides for measles prophylaxis when delivered intranasally opens a new avenue for rapid protection against highly contagious MV infection in a world waiting for measles eradication.

Example 6—Peptide Inhibitors of Human Parainfluenza Virus Type 3, Nipah Virus, and Ebola Virus Based on the results obtained with tocopherol-conjugated peptides for MV described above, it was decided to further investigate the potential of this new lipid moiety in enhancing fusion inhibition of Human parainfluenzae virus type 3 ("HPIV3"), Ebola virus zaire ("ZEBOV") and Nipah virus ("NiV"). The rational of these investigations is based on: (i) the capacity of tocopherol to target brain, lungs and liver; (ii) the antioxidant/antiviral properties of this vitamin which could ameliorate peptides effect; and (iii) the already known capacity of modulating the immune system in the context of viral induced encephalitis.

Figure 5:
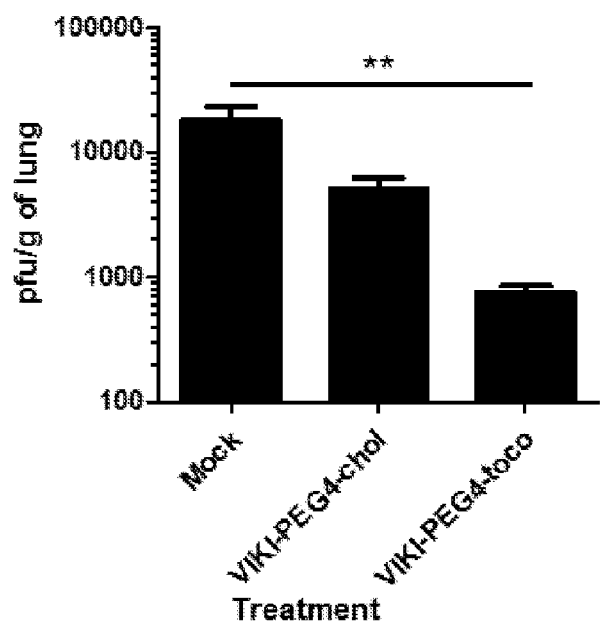
FIG. 5 shows a comparison of cholesterol conjugated peptides (SEQ ID NO: 8) and tocopherol conjugated (SEQ ID NO: 9) peptides as prophylactic treatments against HPIV3. 6-10 week old cotton rats were treated by intraperitoneal injections of the indicated peptides (twice a day, 5 mg/kg) for 3 days after infection with HPIV3. After 3 days, rats were culled and lungs collected for viral titration. Viral titers were determined as previously described (Palermo et al., "Human Parainfluenza Virus Infection of the Airway Epithelium: The Viral Hemagglutinin-Neuraminidase Regulates Fusion Protein Activation and Modulates Infectivity," J. Virol. 83:6900-6908 (2009), which is hereby incorporated by reference in its entirety). VIKI-PEG4-tocopherol significantly reduced the total amount of virus present in the lungs (Kruskal-Wallis one-way ANOVA test, **pvalue=0.0073)
Figure 6:
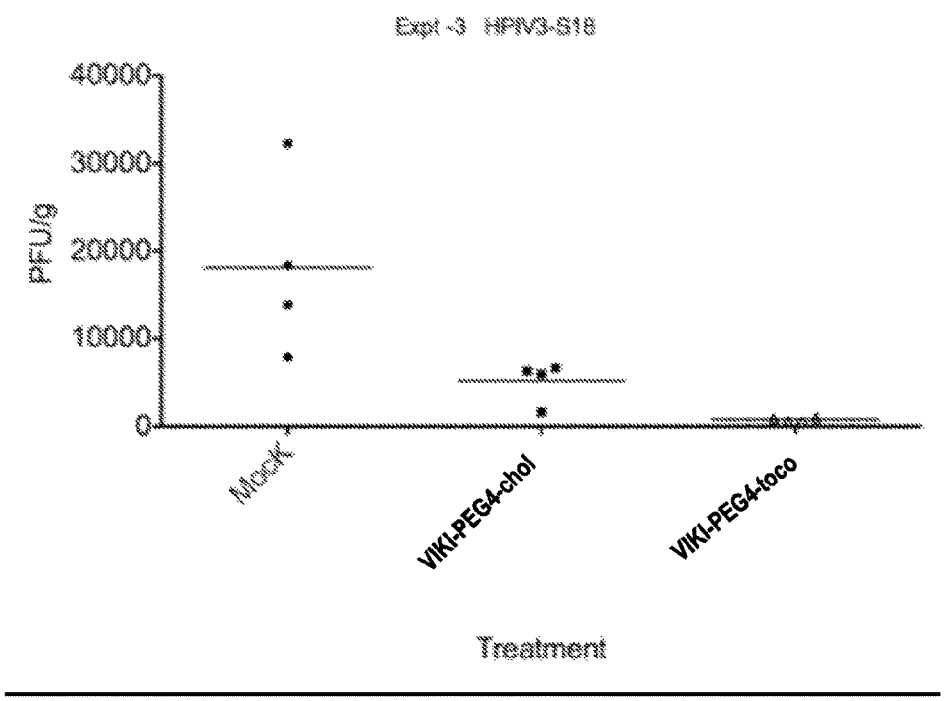
FIG. 6 shows a comparison of prophylactic treatments against HPIV3 using either VIKI-PEG$_4$-cholesterol peptides (SEQ ID NO: 8) or VIKI-PEG$_4$-tocopherol peptides (SEQ ID NO: 9).

It has previously been reported that cholesterol linked to fusion inhibitors to HPIV3 and Nipah virus improves the efficacy of these inhibitors (Palermo et al., "Human Parainfluenza Virus Infection of the Airway Epithelium: Viral Hemagglutinin-Neuraminidase Regulates Fusion Protein Activation and Modulates Infectivity," *J. Virol.* (13): 6900-8 (2009), which is hereby incorporated by reference in its entirety). To investigate tocopherol-conjugated peptides as a prophylactic treatment against HPIV3, these same inhibitors were linked to tocopherol as described in Example 1 and tested in vivo in 6-10 week old cotton rats. The amino acid sequence and in vitro efficacy of these inhibitors are as in (Porotto et al., "Inhibition of Nipah Virus Infection In Vivo: Targeting an Early Stage of Paramyxovirus Fusion Activation during Viral Entry," *PLoS Pathog.* 6(10):e1001168 (2010), which is hereby incorporated by reference in its entirety). These animals were treated by intraperitoneal injections of either VIKI-PEG4-cholesterol or VIKI-PEG4-tocopherol (twice a day, 5 mg/kg) for 3 days after infection with HPIV3. After 3 days, rats were culled and lungs collected for viral titration. Viral titers were determined as previously described (Palermo et al., "Human Parainfluenza Virus Infection of the Airway Epithelium: The Viral Hemagglutinin-Neuraminidase Regulates Fusion Protein Activation and Modulates Infectivity," *J. Virol.* 83:6900-6908 (2009), which is hereby incorporated by reference in its entirety). As shown in FIG. 5, the VIKI-PEG4-tocopherol significantly reduced the total amount of virus present in the lungs in these animals. FIG. 6 shows that the tocopherol-conjugate is more effective than the corresponding cholesterol conjugate.

To broaden the efficacy against human parainfluenza and other viruses including respiratory syncytial virus ("RSV") a modified peptide was designed that would treat both viruses simultaneously. As shown in Table 1, the efficacy of the new peptides VIQKI-PEG24-chol (SEQ ID NO: 18) and VIQKI-PEG24-toc (SEQ ID NO: 19) is an improved inhibitor for HPIV3 compared to its VIKI counterparts, and more importantly the VIQKI peptide is a potent inhibitor compared to RSV. These new peptides were also more potent than the corresponding peptide derived from RSV's own fusion protein (FIG. 16). FIG. 16 shows inhibition of envelope glycoprotein-mediated fusion by VIQKI peptides. This peptide is thus effective compared to three different viruses (HPIV3, Nipah, RSV).

TABLE 1

In Vitro Efficacy of Peptides VIQKI-PEG24-chol and VIQKI-PEG24-toc

| peptide | Sequence and modifications | in vitro efficacy | |
|---|---|---|---|
| | | $IC_{50}$ nM | $IC_{90}$ nM |
| VG | Ac-VALDPIDISIVLNKAKSDLEESKEWIRRSNGKLDSI-GSGSG-C-NH$_2$ (SEQ ID NO: 4) | >1000 | >1000 |
| VG-chol | Ac-VALDPIDISIVLNKAKSDLEESKEWIRRSNGKLDSI-GSGS-C(chol)-NH$_2$ (SEQ ID NO: 5) | 500 | >1000 |
| VG-PEG$_4$-chol | Ac-VALDPIDISIVLNKAKSDLEESKEWIRRSNGKLDSI-GSGS-C(PEG$_4$-chol)-NH$_2$ (SEQ ID NO: 6) | 10 | 100 |
| VG-PEG$_{24}$-chol | Ac-VALDPIDISIVLNKAKSDLEESKEWIRRSNGKLDSI-GSGS-C(PEG$_{24}$-chol)-NH$_2$ (SEQ ID NO: 7) | 0.5 | 50 |
| VIKI-PEG$_4$-chol | Ac-VALDPIDISIVLNKIKSDLEESKEWIRRSNKILDSI-GSGSG-C(PEG$_4$-chol)-NH$_2$ (SEQ ID NO: 8) | 1 | 10 |
| VIKI-PEG$_4$-toc | Ac-VALDPIDISIVLNKIKSDLEESKEWIRRSNKILDSI-GSGSG-C(PEG$_4$-toc)-NH$_2$ (SEQ ID NO: 9) | 3 | 100 |
| VIKI-PEG$_4$-palm | Ac-VALDPIDISIVLNKIKSDLEESKEWIRRSNKILDSI-GSGSG-C(PEG$_4$-palm)-NH$_2$ (SEQ ID NO: 10) | 400 | >1000 |
| VIKI-PEG$_4$-25$^{OH}$chol | Ac-VALDPIDISIVLNKIKSDLEESKEWIRRSNKILDSI-GSGSG-C(PEG$_4$-25$^{OH}$chol)-NH$_2$ (SEQ ID NO: 11) | 55 | >1000 |
| VIKI-PEG$_4$-C20 | Ac-VALDPIDISIVLNKIKSDLEESKEWIRRSNKILDSI-GSGSG-C(PEG$_4$-C20)-NH$_2$ (SEQ ID NO: 12) | 75 | 900 |
| VIKI-PEG$_4$-C30 | Ac-VALDPIDISIVLNKIKSDLEESKEWIRRSNKILDSI-GSGSG-C(PEG$_4$-C30)-NH$_2$ (SEQ ID NO: 13) | 40 | 800 |
| VIKI-PEG$_4$-Betulinic | Ac-VALDPIDISIVLNKIKSDLEESKEWIRRSNKILDSI-GSGSG-C(PEG$_4$-Betulinic)-NH$_2$ (SEQ ID NO: 14) | 550 | >1000 |
| VIKI-PEG$_4$-Ursolic | Ac-VALDPIDISIVLNKIKSDLEESKEWIRRSNKILDSI-GSGSG-C(PEG$_4$-Ursolic)-NH$_2$ (SEQ ID NO: 15) | 200 | >1000 |
| VIKI-PEG$_{24}$-chol | Ac-VALDPIDISIVLNKIKSDLEESKEWIRRSNKILDSI-GSGSG-C(PEG$_{24}$-chol)-NH$_2$ (SEQ ID NO: 16) | 0.3 | 3 |

TABLE 1-continued

In Vitro Efficacy of Peptides VIQKI-PEG24-chol and VIQKI-PEG24-toc

| peptide | Sequence and modifications | in vitro efficacy IC$_{50}$ nM | IC$_{90}$ nM |
|---|---|---|---|
| VIKI-PEG$_{24}$-toc | Ac-VALDPIDISIVLNKIKSDLEESKEWIRRSNKILDSI-GSGSG-C(PEG$_{24}$-toc)-NH$_2$ (SEQ ID NO: 17) | 2 | 80 |
| VIQKI-PEG$_{24}$-chol | Ac-VALDPIDISIVLNKIKSQLEESKEWIRRSNKILDSI-GSGSG-C(PEG$_{24}$-chol)-NH$_2$ (SEQ ID NO: 18) | <0.5 | 1 |
| VIQKI-PEG$_{24}$-toc | Ac-VALDPIDISIVLNKIKSQLEESKEWIRRSNKILDSI-GSGSG-C(PEG$_{24}$-toc)-NH$_2$ (SEQ ID NO: 19) | 1 | 10 |

*In vitro efficacy refers to fusion assay with HPIV3 envelope glycoproteins. Ac is an acetyl group.

To investigate tocopherol-conjugated peptides as a therapeutic treatment against NiV infection, 8 week old Syrian golden hamsters were treated by daily intraperitoneal (i.p.) injections of indicated peptides (2 mg/kg) from the day 1 to day 10 post infection with NiV (500LD$_{50}$, i.p.). Control animals (Mock) were injected with vehicle used to dissolve peptides. As shown in FIG. 7, survival was only observed in the group treated with tocopherol-conjugated peptide.

To investigate tocopherol-conjugated peptides as a prophylactic treatment against a filovirus (e.g., Ebola virus), 5-6 week old BALB/c mice were daily treated by intraperitoneal (i.p.) injections of indicated peptides (10 mg/kg) from the day prior to day 15 post infection with 1000LD$_{50}$ of Ebola virus mouse adapted Zaire strain (ZEBOV, i.p.). As shown in FIG. 8, tocopherol conjugation significantly improved peptide ability to protect from EBOV infection.

Figures 9, 10A, 10B:
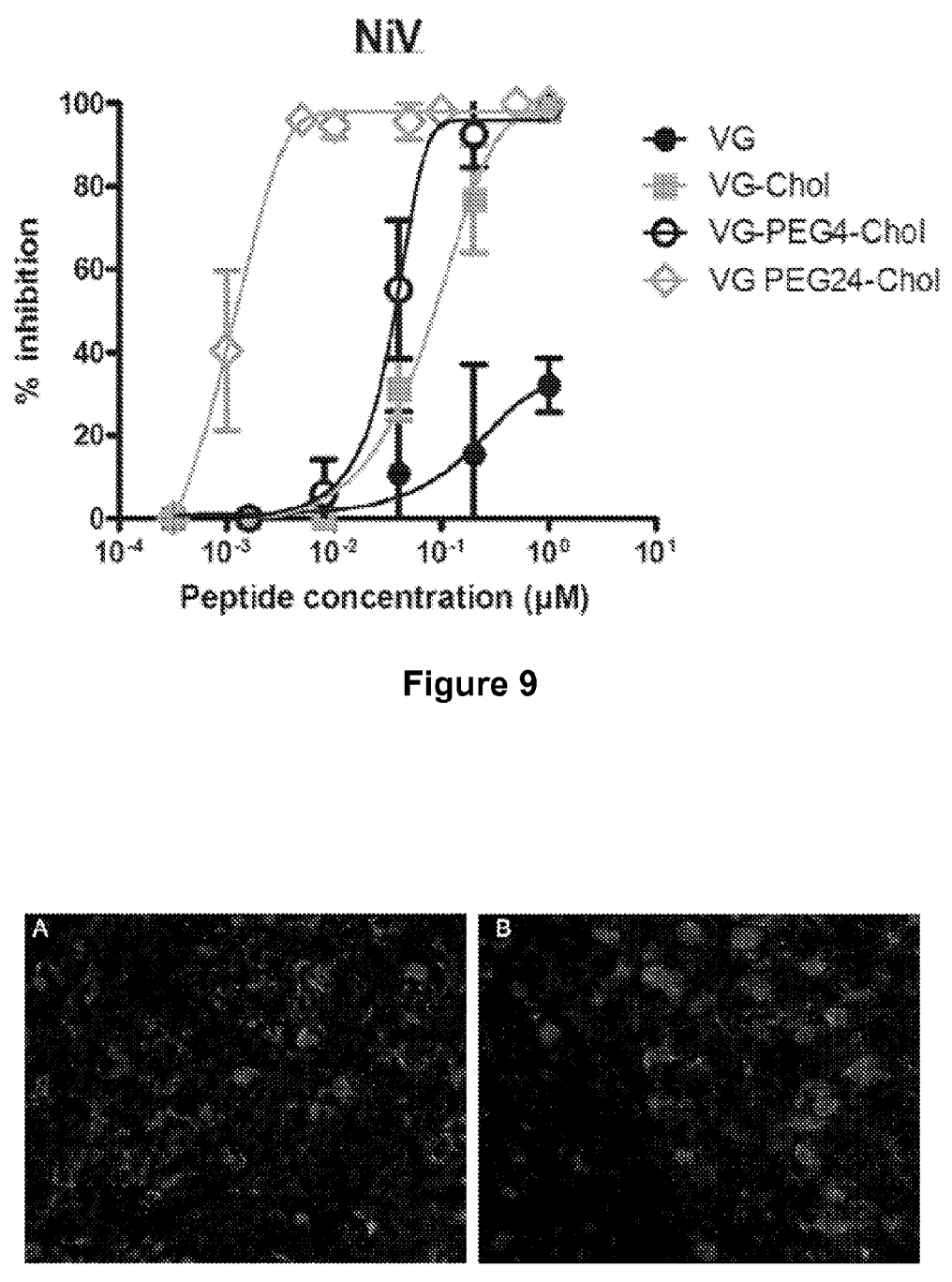

Example 7—Effect of Spacer Between Peptide Fusion Inhibitor and Membrane Binding Portion The importance of the spacer linker between the viral peptide fusion inhibitor and the membrane binding lipid can be demonstrated by observing the changes in the antiviral efficacy first when a spacer is added to a peptide conjugated with a lipid, and second as the size of this spacer increases. FIG. 9 displays the changes in the efficacy of the VG peptide inhibitor of NiV exhibited as a result of these spacer changes. These experiments were carried out in a classic plaque assay. Serial dilutions of peptides were added to sub-confluent monolayer of Vero cells in 6 well plates 30 minutes before infection with NiV (100 PFU/well). After 1 hour at 37° C., medium was replaced by very low viscosity carboxymethylcellulose 4% in DMEM-SVF3%. After 3 to 4 days, plaques were revealed using classic crystal violet method. Similar results were observed with peptide fusion inhibitors of HPIV3 and with MV HRC against MV.

Example 8—Ability of the Peptide Inhibitors to Cross the Blood Brain Barrier

Because of the CNS tropism of MV and NiV, a study was undertaken to determine the ability of the fusion inhibitors presented here to cross the blood brain barrier ("BBB"). Mice were subcutaneously injected with either VIKI-PEG4-Cholesterol or VIKI-PEG4-Tocopherol, 2 mg/kg in water for injection. After 8 hours, animals were euthanized, and brains were collected and directly frozen in isopentane on dry ice for cryopreservation. Samples were then cut and stained as described elsewhere (Welsch et al., "Fatal Measles Virus Infection Prevented by Brain-Penetrant Fusion Inhibitors," J. Virol. 87(24):13785-94 (2013), which is hereby incorporated by reference in its entirety). FIG. 10 shows that these peptides linked to either cholesterol (FIG. 10A) or tocopherol (FIG. 10B) are present in the brain.

In the pharmacokinetic analysis of peptide biodistribution, similar concentrations of all peptides in the brain of injected mice/hamsters were observed after 8 hours. In contrast, immunofluorescent staining shown in FIG. 11 clearly indicates a stronger signal in the brain in the animals that had been injected with peptide having a longer spacer between the peptide and the lipid membrane anchor suggesting a better access to the peptides which could be related to their antiviral potency. The exposure here is the same as in FIG. 10. This observation strengthens the idea that peptides with a longer PEG chain linker might be more accessible and thus more efficient.

Figures 11A, 12:
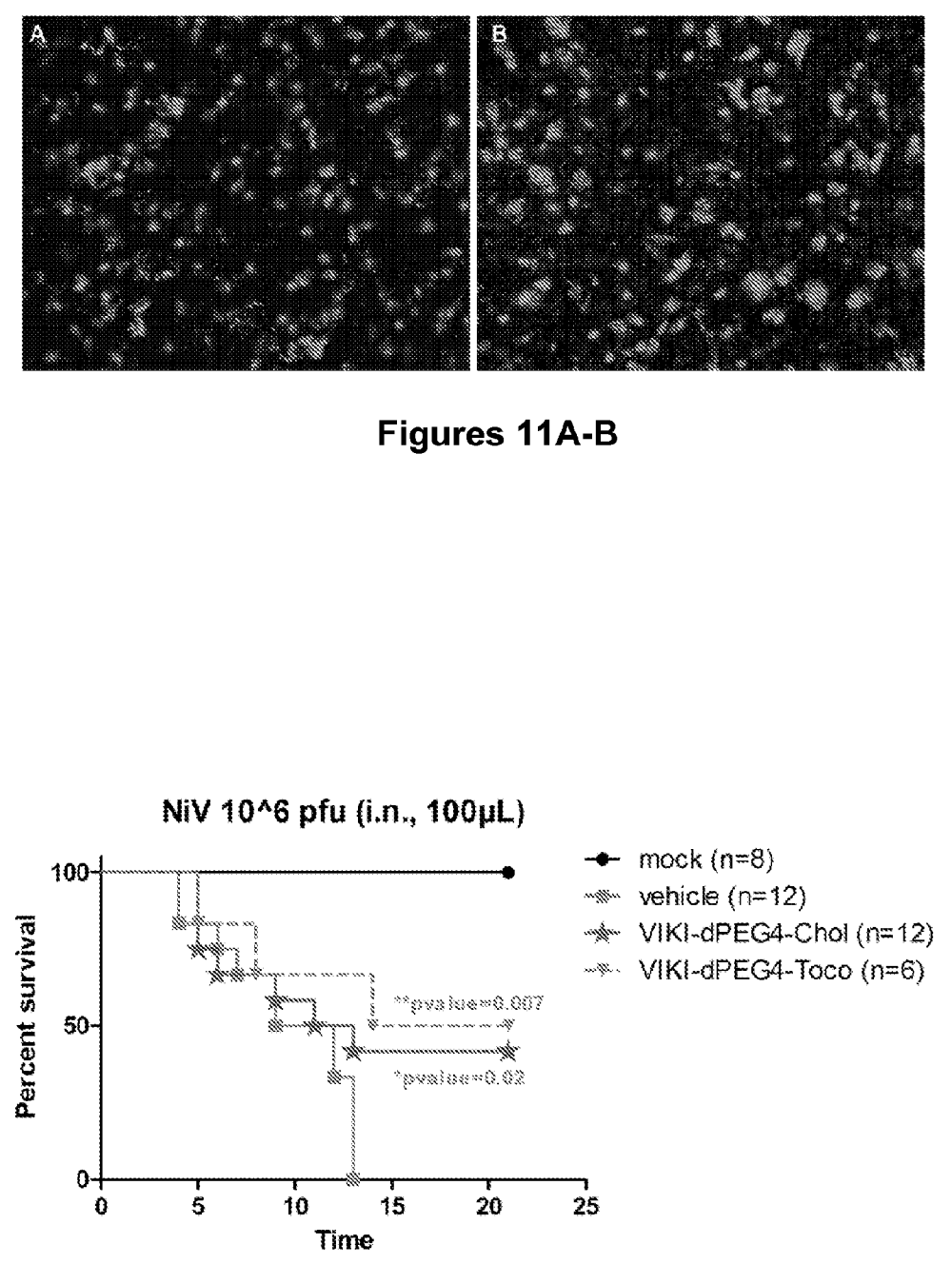

Example 9—Intranasal Administration of HRC Peptides Prevent Hamsters from Highly Lethal NiV Infection In Bangladesh, human NiV infection generally follows the consumption of contaminated food or Oro-nasal transmission from human to human. In hamsters intranasal infection with NiV led to the CNS invasion starting from the olfactive bulb prior to the development of fatal encephalitis. Thus, it was decided to assess the intranasal preventive/protective potency of HPIV3 HRC derived peptide against huge infectious intranasal doses of NiV in hamsters. Eight week old Syrian golden hamsters were given daily intranasal (i.n., 100 µL) administrations of indicated peptides (2 mg/kg) from the day −1 to day 1 post infection with NiV (106 pfu, i.n.). The results in FIG. 12 show that the group of hamsters treated with the tocopherol conjugated peptide survived the NiV infection best.

Example 10—Design of Filovirus Entry Inhibitors

The HRN and HRC regions of filovirus GP2 are connected by a 25-residue linker, containing a CX6CC motif and the internal fusion loop (Collaborative Computational Project No. 4, "The CCP4 Suite: Programs for X-ray Crystallography," *Acta Crystallogr. D.* 50:760-763 (1994) and Dolnik et al., "Filoviruses: Interactions with the Host Cell," *Cell Mol. Life Sci.* 65:756-776 (2008), which are hereby incorporated by reference in their entirety). The structural determination of the fusion core of Ebola GP2 (Bechara et al., "Cell-Penetrating Peptides: 20 Years Later, Where do we Stand?" *FEBS Lett.* 587:1693-1702 (2013); Delos et al., "Studies of the "Chain Reversal Regions" of the Avian Sarcoma/Leukosis Virus (ASLV) and Ebolavirus Fusion Proteins: Analogous Residues are Important, and a His Residue Unique to EnvA Affects the pH Dependence of ASLV Entry," *J. Virol.* 84:5687-5694 (2010); and Diederich et al., "Role of Endocytosis and Cathepsin-Mediated Activation in Nipah Virus Entry," *Virology* 375:391-400 (2008), which are hereby incorporated by reference in their entirety) led to the proposed use of peptides derived from the GP2 C-peptides as antivirals. However, unlike HIV fusion protein-derived C-peptides, the EBOV C-peptides showed low potency (Aguilar et al., "Emerging Paramyxoviruses: Molecular Mechanisms and Antiviral Strategies," *Exp. Rev. Mol. Med.* 13:e6 (2011); Bar et al., "Detection of Cell-Cell Fusion Mediated by Ebola Virus Glycoproteins," *J. Virol.* 80:2815-2822 (2006); Brunger et al., "Crystallography & NMR System: A New Software Suite for macromolecular Structure Determination," *Acta Crystallogr. D. Biol. Crystallogr.* 54:905-921 (1998); and Cote et al., "Small Molecule Inhibitors Reveal Niemann-Pick C1 is Essential for Ebola Virus Infection," *Nature* 477:344-348 (2011), which are hereby incorporated by reference in their entirety), in agreement with the hypothesis that their target was accessible only in the endosome and not at the cell surface. Influenza HA-derived inhibitory peptides were developed that were conjugated to a cholesterol group that localizes them to the cell membrane where fusion occurs (Basler et al., "Evasion of Interferon Responses by Ebola and Marburg Viruses," *J. Interferon. Cytokine Res.* 29:511-520 (2009), which is hereby incorporated by reference in its entirety).

It has previously been shown that the human parainfluenza 3 ("hPIV-3") F derived C-peptides are also effective inhibitors of Ebola GP pseudotype infection. Without the cholesterol tag, the peptides were ineffective. Control C-peptides derived from the same HRC domain and with the same length as the hPIV3 derived C-peptide but based on the amino acid sequence of the respiratory syncytial virus ("RSV") fusion protein were also ineffective. These data suggest that (i) the cholesterol moiety allows the inhibitor to "travel" with the virus into the endosomal compartment, where it can access its target following fusion activation and (ii) the inhibitory activity requires the hPIV3 sequence. Recently, conjugation of a sequence derived from HIV TAT to a fusion inhibitor of Ebola virus improved the antiviral activity of GP2-derived C-peptides (Bente et al., "Disease Modeling for Ebola and Marburg Viruses," *Dis. Model Mech.* 2:12-17 (2009), which is hereby incorporated by reference in its entirety) but also in this case the $IC_{50}$ was around 50 uM. The HIV TAT sequence was added to improve the localization of the HRC peptides into the cells. Several other peptides have been described (Brecher et al., "Cathepsin Cleavage Potentiates the Ebola Virus Glycoprotein to Undergo a Subsequent Fusion-Relevant Conformational Change," *J. Virol.* 86:364-372 (2012), which is hereby incorporated by reference in its entirety) to improved intracellular localization, therefore in parallel with the TAT sequence the C105Y peptide sequence was tested since it has been shown to be effective for intracellular delivery (Coker et al., "Emerging Infectious Diseases in Southeast Asia: Regional Challenges to Control," *Lancet* 377:599-609 (2011), which is hereby incorporated by reference in its entirety). Based on these findings a series of lipid modified hPIV3 F and EBOLA ZAIRE (ZEBOV) GP-derived peptides was designed and produced. The lipid moieties and the polyethylene glycol ("PEG") 4 spacer are located in the C-terminus of the peptide. Two control peptides were used bearing the same linkers and lipid modifications but with the HRC region derived from feline immunodeficiency virus ("FIV") envelope HRC region (FIV-dPEG4-Chol and FIV-dPEG4-Toc).

Example 11—Inhibition of Filovirus GP Mediated Infectivity In Vitro

The ability of the C-peptides to inhibit GPs mediated infection using a previously established VSV-based pseudotype multicycle replication assay are shown in Table 2 (Carette et al., "Ebola Virus Entry Requires the Cholesterol Transporter Niemann-Pick C1," *Nature* 477:340-343 (2011) and Coppola et al., "Identification of Inhibitors Using a Cell-Based Assay for Monitoring Golgi-Resident Protease Activity," *Anal. Biochem.* 364:19-29 (2007), which are hereby incorporated by reference in their entirety). It has been shown that this pseudotype based assay is more stringent compared to standard single cycle pseudotype assay in the ability to detect the most potent entry inhibitor for several different envelope viruses (Colman et al., "The Structural Biology of Type I Viral Membrane Fusion," *Nat. Rev. Mol. Cell Biol.* 4:309-319 (2003) and Coppola et al., "Identification of Inhibitors Using a Cell-Based Assay for Monitoring Golgi-Resident Protease Activity," *Anal. Biochem.* 364:19-29 (2007), which are hereby incorporated by reference in their entirety). As expected and shown in Table 2, the lipid-derivatized TAT-hPIV3 and TAT-EBOLA-HRC-peptides are more potent than their unconjugated counterparts. Control EBOLA C-peptides derived from the same HRC domain but without the TAT sequence were also ineffective even when lipid conjugated (10 uM was the highest concentration tested since only peptides with low micromolar/nanomolar concentration effectiveness can be candidates for in vivo study). Finally the FIV peptides (that are very potent against the FIV virus) with the same linker and lipid moiety were not effective, indicating that the activity could not be attributed to the lipid moiety alone. These data suggest that the inhibitory activity requires both the TAT sequence and the lipid conjugation. At the concentration used antiviral activity was observed against pseudotype virions bearing the VSV G envelope glycoprotein. The ability of both the hPIV3 and EBOV-HRC derived peptide to inhibit also the MARV GP mediated infection (despite the difference in the HRC region, as shown in Table 3) support the likelihood of developing a single broad-spectrum fusion inhibitor for several filoviruses.

TABLE 2

Viral Peptide Inhibitors and Viral Inhibition

| Name | Sequence and modifications | IC$_{50}$UM MARV | IC$_{50}$UM ZEBOV |
|---|---|---|---|
| EBOLA | Ac-IEPHDWTKNITDKIDQIIHDFVDK-GSGSG-C-NH2 (SEQ ID NO: 20) | >10 | >10 |
| EBOLA-dPEG4 | Ac-IEPHDWTKNITDKIDQIIHDFVDK-GSGSG-dPEG4-C-NH2 (SEQ ID NO: 21) | >10 | >10 |
| EBOLA-dPEG4-Chol | Ac-IEPHDWTKNITDKIDQIIHDFVDK-GSGSG-dPEG4-C-(Cholesterol) (SEQ ID NO: 22) | >10 | >10 |
| EBOLA-dPEG4-Toc | Ac-IEPHDWTKNITDKIDQIIHDFVDK-GSGSG-dPEG4-C-(Tocopherol) (SEQ ID NO: 23) | >10 | >10 |
| TAT-EBOLA | Ac-YGRKKRRQRRR-GSG-IEPHDWTKNITDKIDQIIHDFVDK-GSGSG-C-NH2 (SEQ ID NO: 24) | >10 | >10 |
| TAT-EBOLA-dPEG4 | Ac-YGRKKRRQRRR-GSG-IEPHDWTKNITDKIDQIIHDFVDK-GSGSG-dPEG4-C-NH2 (SEQ ID NO: 25) | >10 | >10 |
| TAT-EBOLA-dPEG4-Chol | Ac-YGRKKRRQRRR-GSG-IEPHDWTKNITDKIDQIIHDFVDK-GSGSG-dPEG4-C-(Cholesterol) (SEQ ID NO: 26) | 5.5 | 4.5 |
| TAT-EBOLA-dPEG4-Toc | Ac-YGRKKRRQRRR-GSG-IEPHDWTKNITDKIDQIIHDFVDK-GSGSG-dPEG4-C-(Tocopherol) (SEQ ID NO: 27) | 5 | 4 |
| TAT-HPIV3-dPEG4 | Ac-YGRKKRRQRRR-GSG-VALDPIDISIVLNKAKSDLEESKEWIRRSNGKLDSI-dPEG4-C-NH2 (SEQ ID NO: 28) | >10 | >10 |
| TAT-HPIV3-dPEG4-Chol | Ac-YGRKKRRQRRR-GSG-VALDPIDISIVLNKAKSDLEESKEWIRRSNGKLDSI-dPEG4-C-(Cholesterol) (SEQ ID NO: 29) | 7 | 7 |
| TAT-HPIV3-dPEG4-Toc | Ac-YGRKKRRQRRR-GSG-VALDPIDISIVLNKAKSDLEESKEWIRRSNGKLDSI-dPEG4-C-(Tocopherol) (SEQ ID NO: 30) | 6 | 5 |
| C105-EBOLA-dPEG4 | Ac-PFVYLI-GSG-IEPHDWTKNITDKIDQIIHDFVDK-GSGSG-dPEG4-C-NH2 (SEQ ID NO: 31) | >10 | >10 |
| C105-EBOLA-dPEG4-Chol | Ac-PFVYLI-GSG-IEPHDWTKNITDKIDQIIHDFVDK-GSGSG-dPEG4-C-(Cholesterol) (SEQ ID NO: 32) | >10 | >10 |
| C105-EBOLA-dPEG4-Toc | Ac-PFVYLI-GSG-IEPHDWTKNITDKIDQIIHDFVDK-GSGSG-dPEG4-C-(Tocopherol) (SEQ ID NO: 33) | >10 | >10 |
| FIV-dPEG4-Chol | Ac-WYNQTKDLQQKFYEIIMDIIEQNNVQGKKGIQQLQK-GSGSG-dPEG4-C-(Cholesterol) (SEQ ID NO: 34) | >10 | >10 |
| FIV-dPEG4-Toc | Ac-WYNQTKDLQQKFYEIIMDIIEQNNVQGKKGIQQLQK-GSGSG-dPEG4-C-(Tocopherol) (SEQ ID NO: 35) | >10 | >10 |

Double underlined residues are derived from C105Y peptide;
GSG and (GSG)$_n$ residues are linker regions;
bold residues are from EBOV GP2 or FIV envelope HRCs derived sequence;
dotted underlined residues correspond to the HIV TAT sequence.
The "PFVYLI" sequences in the three C-105 EBOLA peptides are made from D-amino acids.
Ac is an acetyl group.

TABLE 3

The HRC Region of Indicated *Ebolaviruses**

| Zaire Ebola GP2 610-633 | IEPHDWTKNITDKIDQIIHDFVDK (SEQ ID NO: 36) |
|---|---|
| Marburg Lake Victoria-Musoke | IGIEDLSKNISEQIDQIKKDEQKE (SEQ ID NO: 37) |

*Bold, identical residue; underlined, conserved substitution.

Example 12—Inhibition of (MA-)ZEBOV In Vivo

The effectiveness of the peptides in FIG. 13A were confirmed against live virus. The peptides in Table 2 highlighted in grey (TAT and PEG linked Ebola and HPIV3 peptides) were then tested in mice for acute toxicity at 20 mg/ml for 14 days (intraperitoneal delivery), and tolerability issues were not observed. Mouse pharmacokinetic studies were performed by Apredica for the 6 peptides highlighted in Table 3 to confirm sustained plasma presence of the lipid conjugated peptides for at least 24 hours. For the in vivo study presented in FIG. 14, 5-6 week old BALB/c mice were used, 5 animals per group treated from day −1 to day 15 post-infection with 10 mg/kg i.p. (~100 ul isotonic aqueous solution per animal). The animals were infected with 100LD$_{50}$. Significant weight loss was observed for all infected animals. However, 4 out of the 5 animals treated prophylactically with the TAT-EBOLA-dPEG4-Tocopherol survived. Interestingly the TAT-EBOLA-dPEG4 without any lipid moiety treatment partially protected 2 animals out of 5 from the lethal infection. Of the TAT-HPIV3-dPEG4-Tocopherol treated animals only one survived. None of the animals treated with the cholesterol conjugated peptides survived, indicating in this case that cholesterol conjugation was not advantageous for in vivo protection. These data were recently confirmed in a second challenge experiment in which all the surviving animals from the experiment presented in FIG. 2 were re-challenged. All the animals survived the second challenge indicating that the treatment with peptides did not provide sterilizing immunity and allowed for development of protective immunity.

Materials and Methods for Example 13

Biodistribution Analysis:

For biodistribution experiments in cotton rats, the animals received the indicated peptides (6 mg/kg) i.n. in 100 µl of diluent. After 8 hours, blood was collected by intracardiac puncture in EDTA Vacutainer tubes, and sera were conserved at 20° C. until their use in Enzyme-linked immunosorbent assay ("ELISA"). Organs from each animal were collected and conserved at −80° C.

ELISA:

For biodistribution studies, each organ was weighed and mixed in PBS (1:1, wt/vol) using an Ultra-Turrax homogenizer. Samples were then treated with acetonitrile-1% trifluoroacetic acid (TFA), 1:4 (vol/vol), for 1 hour on a rotor at 4° C. and then centrifuged for 10 min at 8,000 rpm. Supernatant fluids were collected, and peptide concentration was determined using an ELISA. Maxisorp 96-well plates (Nunc) were coated overnight with purified rabbit anti-MV FHRCantibodies (5 g/ml) in carbonate/bicarbonate buffer, pH 7.4. Plates were washed twice using PBS followed by incubation with 3% bovine serum albumin ("BSA") in PBS (blocking buffer) for 30 min. The blocking buffer was replaced with 2 dilutions of each sample in 3% PBS-BSA in duplicate, and the mixture was incubated for 90 minutes at RT. After multiple washes in PBS, the peptide was detected using a horseradish peroxidase ("HRP")-conjugated rabbit custom-made anti-MV F HRC antibody (1:1,500) in blocking buffer for 2 h at RT. HRP activity was recorded as absorbance at 492 nm on the Sigmafast OPD substrate system (Sigma-Aldrich) after adding the stop solution. Standard curves were established for each peptide (using the same ELISA conditions as for the test samples), and the detection limit was determined to be 0.15 nM.

Statistical Analysis:

Data are expressed as means and standard deviations ("SD"). Statistical analyses were performed using a Mann-Whitney U test and a Mantel-Cox test and GraphPad Prism software.

Example 13—Prototype Peptide Inhibitors

The monomeric HRC2 and the dimeric HRC4 peptides described in Examples 1-5 were modified by varying the lipid moieties (e.g., tocopherol and $25^{OH}$-cholesterol) (Table 4). Example 6 and FIG. 6 above describe that tocopherol-conjugated fusion peptides are more effective than the corresponding cholesterol conjugated peptides at inhibiting HPIV3 infection in vivo. $25^{OH}$-cholesterol has been suggested to have broad-spectrum activity against a number of enveloped viruses (Liu et al., "Interferon-Inducible Cholesterol-25-Hydroxylase Broadly Inhibits Viral Entry by Production of 25-Hydroxycholesterol," *Immunity* 38:92-105 (2013), which is hereby incorporated by reference in its entirety). Since it has previously been shown that longer linkers increase exposure of the HRC peptide to its target HRN region on F, PEG linker lengths were modified (e.g., $PEG_{24}$) (Augusto et al., "Improvement of HIV Fusion Inhibitor C34 Efficacy by Membrane Anchoring and Enhanced Exposure," *J. Antimicrob. Chemother.* 69:1286-97 (2014), which is hereby incorporated by reference in its entirety). A quantitative assay was used to assess inhibition of fusion. Cells expressing the MV H/F and cells expressing the human CD150 receptor were incubated for 6 hours at 37° C. (Mathieu et al., "Prevention of Measles Virus Infection by Intranasal Delivery of Fusion Inhibitor Peptides," *J. Virol.* 89:1143-55 (2015), which is hereby incorporated by reference in its entirety) in the presence of increasing concentrations of the inhibitor. The $IC_{50}$ and $IC_{90}$ values for the HRC peptides (Table 5) show that modifications significantly increased inhibitory potency. For example the $IC_{90}$ for the cholesterol conjugated monomeric peptide HRC2 (2000 nM) is 50 times higher than that for HRC2-$25^{OH}$-chol (80 nM). The longer linker ($PEG_{24}$) lowers the $IC_{50}$ of the original dimeric HRC4 to 0.1 nM (10-fold improvement).

TABLE 4

Sequences and modifications of MV HRC derived peptides. Highlighted peptides were described in Examples 1-5.

| Name | Sequence and modifications | Fusion Assay (CD150) | |
|---|---|---|---|
| | | $IC_{50}$ nM | $IC_{90}$ nM |
| HRC1 | Ac-PPISLERLDVGTNLGNAIAKLEDAKELLESSDQILR-GSGSG-C-(CH$_2$CONH$_2$)——NH$_2$ ((SEQ ID NO: 38) | ~1000 | ~9000 |
| HRC2 | Ac-PPISLERLDVGTNLGNAIAKLEDAKELLESSDQILR-GSGSG-C-(PEG$_4$-Cholesterol)-NH$_2$ (SEQ ID NO: 39) | 60 ± 10 | ~2000 |
| HRC3 | [Ac-PPISLERLDVGTNLGNAIAKLEDAKELLESSDQILR-GSGSG-C-(MAL-PEG$_{11}$)-NH$_2$]$_2$ (SEQ ID NO: 40) | 440 ± 60 | ~5000 |
| HRC4 | [Ac-PPISLERLDVGTNLGNAIAKLEDAKELLESSDQILR-GSGSG-C-(MAL-PEG$_4$)NH$_2$]$_2$-Cholesterol (SEQ ID NO: 41) | 1 ± 0.5 | ~50 |
| HRC2-$25^{OH}$-Chol | Ac-PPISLERLDVGTNLGNAIAKLEDAKELLESSDQILR-GSGSG-C-(PEG$_4$-$25^{OH}$-Cholesterol)-NH$_2$ (SEQ ID NO: 42) | 7 ± 1 | ~80 |
| HRC4-Toco | [Ac-PPISLERLDVGTNLGNAIAKLEDAKELLESSDQILR-GSGSG-C-(MAL-PEG$_4$)NH$_2$]$_2$-Tocopherol (SEQ ID NO: 43) | 45 ± 20 | ~200 |
| HRC4-PEG$_{24}$-Chol | [Ac-PPISLERLDVGTNLGNAIAKLEDAKELLESSDQILR-GSGSG-C-(MAL-PEG$_{24}$)NH$_2$]$_2$-Cholesterol (SEQ ID NO: 44) | 0.1 ± 0.05 | ~10 |

*Ac is an acetyl group.

To assess peptide biodistribution in the respiratory tract of cotton rats, peptides were delivered intranasally (6 mg/kg, 3 animals) and the animals were euthanized 8 hours after administration. Peptide concentration in serum, lung, and brain were measured by ELISA (shown in log scale in FIG. 14) (Mathieu et al., "Prevention of Measles Virus Infection by Intranasal Delivery of Fusion Inhibitor Peptides," J. Virol. 89:1143-55 (2015), which is hereby incorporated by reference in its entirety). As anticipated (based on previous work (Mathieu et al., "Prevention of Measles Virus Infection by Intranasal Delivery of Fusion Inhibitor Peptides," J. Virol. 89:1143-55 (2015), which is hereby incorporated by reference in its entirety)) most of the peptides remain in the lung, with the HRC4-tocopherol reaching the highest concentration (~2000 nM compared to ~400 nM for the original HRC4 (Mathieu et al., "Prevention of Measles Virus Infection by Intranasal Delivery of Fusion Inhibitor Peptides," J. Virol. 89:1143-55 (2015), which is hereby incorporated by reference in its entirety)). For the HRC4-tocopherol and the HRC4 with $PEG_{24}$ there is minimal presence in the serum and no CNS localization. For the original HRC2 and HRC4, as have been published (Mathieu et al., "Prevention of Measles Virus Infection by Intranasal Delivery of Fusion Inhibitor Peptides," J. Virol. 89:1143-55 (2015), which is hereby incorporated by reference in its entirety), a small fraction of the administered peptides was present in the serum and the brain. The improved HRC2 with $25^{OH}$-cholesterol localizes to the CNS after intranasal delivery (of potential interest for post-infection treatment). Thus, modulation of lipid moiety and/or PEG linker peptide improved antiviral potency and in vivo biodistribution. Moreover, intranasal administration of peptides did not result in any detectable undesirable effects in the cotton rats.

Figure 13:
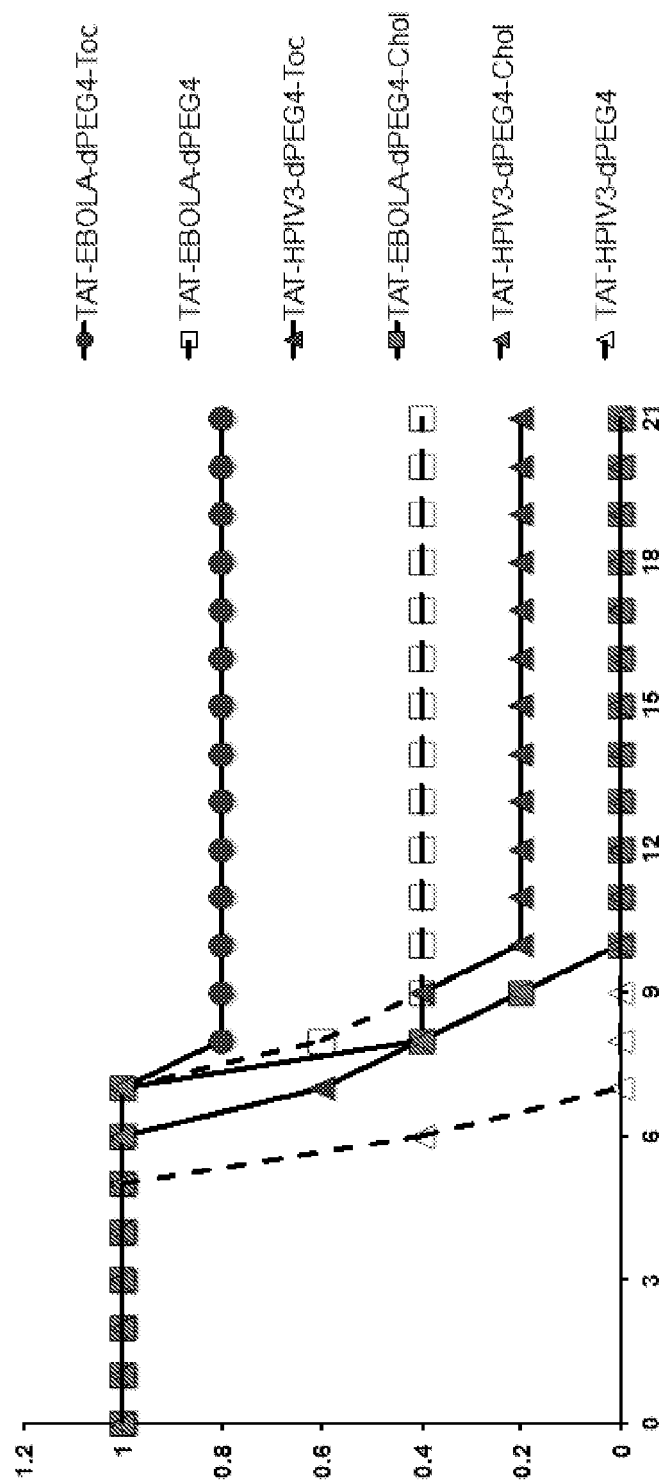
FIG. 13 shows that TAT-EBOLA-dPEG4-tocopherol protects mice from the lethal (MA-)ZEBOV infection. 5-6 weeks old BALB/c mice received the intraperitoneal challenge of MA-EBOV 24 h after the first peptide treatment, and were followed for 5 weeks post infection. Peptide (10 mg/kg dissolved in isotonic water) was administrated i.p. daily for 15 days.
Figures 14A, 14B, 14C:
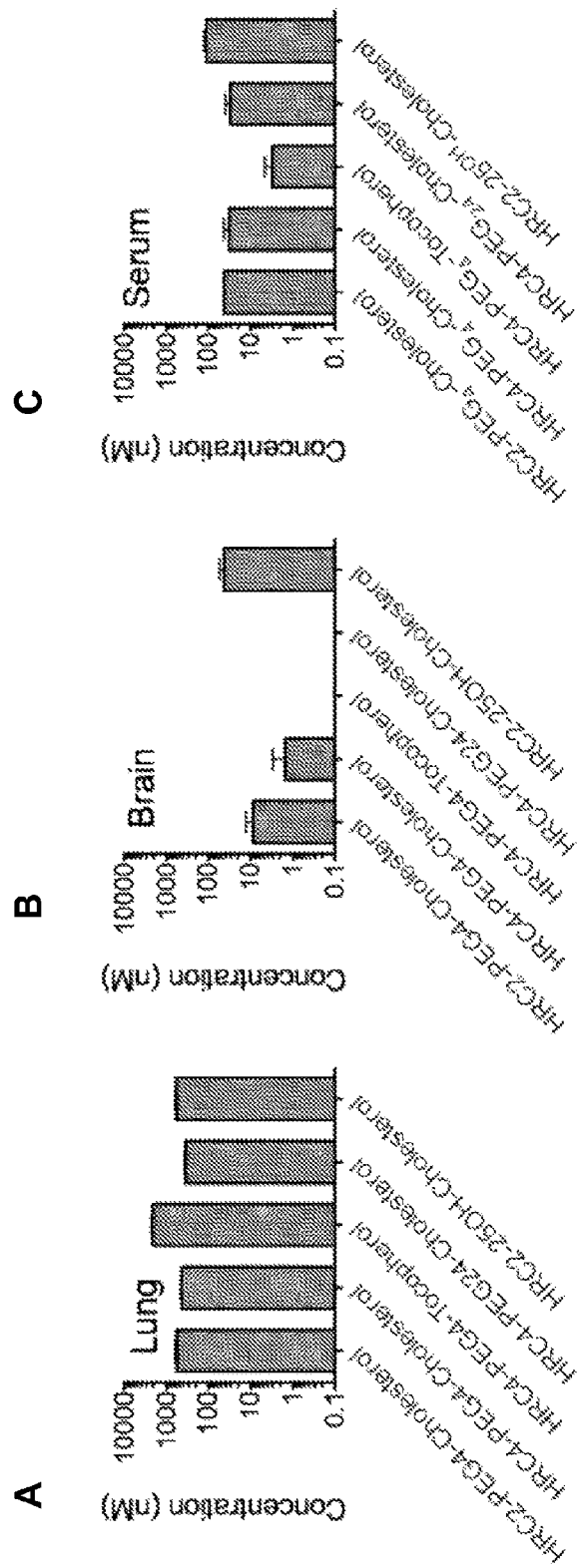
FIGS. 14A-14C show the bioavailability of MV HRC derived peptides in the lung (FIG. 14A), brain (FIG. 14B), and serum (FIG. 14C) of cotton rats, 8 hours after intranasal administration. Data are presented as an average of three animals ±STDEV (150 µl of peptides were administered). Dose: 5 mg/kg.

Example 14—Lipid-Conjugated Inhibitor Peptide Nanoparticles Undergo Cellular Internalization Since the TAT-EBOV-dPEG4-Toco peptide is an effective inhibitor in vivo (see FIG. 13), it was hypothesized that the peptides localize to the endosome where they partition into the endosomal membrane and exert their antiviral activity. To test this hypothesis, the cellular localization of the Ebola-derived peptides was tracked using confocal microscopy (Porotto et al., "Mechanism of Fusion Triggering by Human Parainfluenza Virus Type III: Communication Between Viral Glycoproteins During Entry," J. Biol. Chem. 287:778-93 (2012), which is hereby incorporated by reference in its entirety). The peptides (dissolved in DMSO to 1000 µM) were diluted in PBS to 100 µM, incubated at RT for 30 minutes, and added to live cells at 37° C. at several concentrations. Peptides conjugated with cholesterol and peptides conjugated with tocopherol ("Toc") were tested. Controls included peptides without lipids and DMSO alone. Cells were fixed, permeabilized with 0.02% Tween-20 in PBS, stained with custom made biotin-conjugated anti-peptide antibodies and with DAPI (for nuclei). The anti-peptide antibodies were detected with streptavidin-phyco-erythrin ("PE"). Fluorescence of PE (emission 580 nm) and DAPI (emission 460 nm) was acquired as previously described (Porotto et al., "Mechanism of Fusion Triggering by Human Parainfluenza Virus Type III: Communication Between Viral Glycoproteins During Entry," J. Biol. Chem. 287:778-93 (2012), which is hereby incorporated by reference in its entirety). FIGS. 15A-G shows incubation for 60' at 10 µM concentrations. The intense spots inside the cells indicate intracellular localization of the TAT-EBOV-dPEG4-Toc. The TAT-EBOV-dPEG4-Chol remains localized at the cell surface with some intracellular localization. The EBOV-PEG4-Chol (without TAT) remains mostly localized on the cell membrane with minimal cellular internalization. The TAT-EBOV is present both at the cell membrane and inside the cells. FIGS. 15A-G shows that only peptides with both the CPP sequence (i.e., TAT) and the lipid moiety are delivered intracellularly. These findings support the hypothesis that EBOV-derived peptides require both features to be effective in vivo (FIG. 13).

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed:

1. An inhibitor of fusion between a viral membrane from an enveloped virus and a cell membrane, wherein the viral membrane comprises a fusion mediating protein including a C-terminal peptide, said inhibitor comprising:
   the C-terminal peptide of the fusion mediating protein from an enveloped virus and
   tocopherol or a derivative or pharmaceutically acceptable salt thereof attached to the C-terminal peptide, wherein the C-terminal peptide is dimerized.

2. The inhibitor of claim 1, wherein the C-terminal peptide is a Type I viral fusogenic peptide.

3. The inhibitor of claim 1, wherein the C-terminal peptide is covalently or non-covalently bound to the tocopherol or derivative or pharmaceutically acceptable salt thereof.

4. The inhibitor of claim 1 further comprising:
   a linker coupling the C-terminal peptide and the tocopherol or the derivative or pharmaceutically acceptable salt thereof.

5. The inhibitor of claim 4, wherein the linker is selected from the group consisting of a peptide of two or more amino acids and one or more polyethylene glycol oligomer moieties.

6. The inhibitor of claim 5, wherein the linker comprises one or more polyethylene glycol oligomer moieties having a formula of —(OCH$_2$CH$_2$)$_m$—, wherein m is an integer 1 to 24.

7. The inhibitor of claim 1 further comprising:
an immunogenic carrier molecule linked to the C-terminal peptide or to the tocopherol, tocopherol derivative, or a pharmaceutically acceptable salt thereof.

8. A pharmaceutical composition comprising:
the inhibitor of claim 1 and
an adjuvant.

9. The inhibitor of claim 1 further comprising:
a cell penetrating peptide linked to the C-terminal peptide, wherein the cell penetrating peptide is selected from the group consisting of YGRKKRRQRRR (SEQ ID NO: 2) and PFVYLI (SEQ ID NO: 3).

10. The inhibitor of claim 1, wherein the C-terminal peptide is an HRC peptide.

11. The inhibitor of claim 10, wherein the HRC peptide is derived from a virus selected from the group consisting of Measles virus, Ebola virus, Human parainfluenza virus, Nipah virus, and HIV-1.

12. The inhibitor of claim 11, wherein the HRC peptide is derived from Measles virus and the inhibitor is selected from the group consisting of MV HRC5 and MV HRC6.

13. The inhibitor of claim 11, wherein the HRC peptide is derived from Human parainfluenza virus and the inhibitor is VIKI-PEG4-tocopherol.

14. The inhibitor of claim 11, wherein the HRC peptide is derived from Nipah virus and the inhibitor is VIKI-PEG4-tocopherol.

15. The inhibitor of claim 11, wherein the HRC peptide is derived from Ebola virus and the inhibitor is TAT-Ebola-PEG4-toco.

16. The inhibitor of claim 1, wherein the inhibitor includes tocopherol, wherein the tocopherol is selected from the group consisting of alpha-tocopherol, beta-tocopherol, gamma-tocopherol, and delta-tocopherol.

17. A method of inhibiting viral fusion in a subject comprising:
selecting a subject infected with or at risk of being infected with a virus and
administering to the selected subject the inhibitor of claim 1 under conditions effective to inhibit viral fusion.

18. A method of blocking measles viral spread in a subject comprising:
selecting a subject infected with or at risk of being infected with a measles virus and
administering to the selected subject the inhibitor of claim 1 under conditions effective to block measles viral spread.

* * * * *

SEQUENCE LISTING

```
<160> NUMBER OF SEQ ID NOS: 38

<210> SEQ ID NO 1
<211> LENGTH: 42
<212> TYPE: PRT
<213> ORGANISM: Artificial
<220> FEATURE:
<223> OTHER INFORMATION: Measles Virus HRC1 peptide derived from
      C-terminal heptad repeat region

<400> SEQUENCE: 1

Pro Pro Ile Ser Leu Glu Arg Leu Asp Val Gly Thr Asn Leu Gly Asn
1               5                   10                  15

Ala Ile Ala Lys Leu Glu Asp Ala Lys Glu Leu Leu Glu Ser Ser Asp
            20                  25                  30

Gln Ile Leu Arg Gly Ser Gly Ser Gly Cys
        35                  40

<210> SEQ ID NO 2
<211> LENGTH: 11
<212> TYPE: PRT
```

```
<213> ORGANISM: Artificial
<220> FEATURE:
<223> OTHER INFORMATION: HIV-1 Tat Peptide

<400> SEQUENCE: 2

Tyr Gly Arg Lys Lys Arg Arg Gln Arg Arg Arg
1               5                   10

<210> SEQ ID NO 3
<211> LENGTH: 6
<212> TYPE: PRT
<213> ORGANISM: Artificial
<220> FEATURE:
<223> OTHER INFORMATION: C105Y peptide

<400> SEQUENCE: 3

Pro Phe Val Tyr Leu Ile
1               5

<210> SEQ ID NO 4
<211> LENGTH: 44
<212> TYPE: PRT
<213> ORGANISM: Artificial
<220> FEATURE:
<223> OTHER INFORMATION: VG peptide
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (44)..(44)
<223> OTHER INFORMATION: X at position 44 is NH2

<400> SEQUENCE: 4

Xaa Val Ala Leu Asp Pro Ile Asp Ile Ser Ile Val Leu Asn Lys Ala
1               5                   10                  15

Lys Ser Asp Leu Glu Glu Ser Lys Glu Trp Ile Arg Arg Ser Asn Gly
            20                  25                  30

Lys Leu Asp Ser Ile Gly Ser Gly Ser Gly Cys Xaa
        35                  40

<210> SEQ ID NO 5
<211> LENGTH: 43
<212> TYPE: PRT
<213> ORGANISM: Artificial
<220> FEATURE:
<223> OTHER INFORMATION: VG-chol peptide
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (43)..(43)
<223> OTHER INFORMATION: X at position 43 is (chol)-NH2

<400> SEQUENCE: 5

Xaa Val Ala Leu Asp Pro Ile Asp Ile Ser Ile Val Leu Asn Lys Ala
1               5                   10                  15

Lys Ser Asp Leu Glu Glu Ser Lys Glu Trp Ile Arg Arg Ser Asn Gly
            20                  25                  30

Lys Leu Asp Ser Ile Gly Ser Gly Ser Cys Xaa
        35                  40

<210> SEQ ID NO 6
<211> LENGTH: 43
```

```
<212> TYPE: PRT
<213> ORGANISM: Artificial
<220> FEATURE:
<223> OTHER INFORMATION: VG-PEG4-chol peptide
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (43)..(43)
<223> OTHER INFORMATION: X at position 43 is (PEG4-chol)-NH2

<400> SEQUENCE: 6

Xaa Val Ala Leu Asp Pro Ile Asp Ile Ser Ile Val Leu Asn Lys Ala
1               5                   10                  15

Lys Ser Asp Leu Glu Glu Ser Lys Glu Trp Ile Arg Arg Ser Asn Gly
            20                  25                  30

Lys Leu Asp Ser Ile Gly Ser Gly Ser Cys Xaa
        35                  40

<210> SEQ ID NO 7
<211> LENGTH: 43
<212> TYPE: PRT
<213> ORGANISM: Artificial
<220> FEATURE:
<223> OTHER INFORMATION: VG-PEG24-chol peptide
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (43)..(43)
<223> OTHER INFORMATION: X at position 43 is (PEG24-chol)-NH2

<400> SEQUENCE: 7

Xaa Val Ala Leu Asp Pro Ile Asp Ile Ser Ile Val Leu Asn Lys Ala
1               5                   10                  15

Lys Ser Asp Leu Glu Glu Ser Lys Glu Trp Ile Arg Arg Ser Asn Gly
            20                  25                  30

Lys Leu Asp Ser Ile Gly Ser Gly Ser Cys Xaa
        35                  40

<210> SEQ ID NO 8
<211> LENGTH: 44
<212> TYPE: PRT
<213> ORGANISM: Artificial
<220> FEATURE:
<223> OTHER INFORMATION: VIKI-PEG4-chol peptide
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (44)..(44)
<223> OTHER INFORMATION: X at position 44 is (PEG4-chol)-NH2

<400> SEQUENCE: 8

Xaa Val Ala Leu Asp Pro Ile Asp Ile Ser Ile Val Leu Asn Lys Ile
1               5                   10                  15

Lys Ser Asp Leu Glu Glu Ser Lys Glu Trp Ile Arg Arg Ser Asn Lys
            20                  25                  30

Ile Leu Asp Ser Ile Gly Ser Gly Ser Gly Cys Xaa
        35                  40
```

```
<210> SEQ ID NO 9
<211> LENGTH: 44
<212> TYPE: PRT
<213> ORGANISM: Artificial
<220> FEATURE:
<223> OTHER INFORMATION: VIKI-PEG4-toc peptide
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (44)..(44)
<223> OTHER INFORMATION: X at position 44 is (PEG4-toc)-NH2

<400> SEQUENCE: 9

Xaa Val Ala Leu Asp Pro Ile Asp Ile Ser Ile Val Leu Asn Lys Ile
1               5                   10                  15

Lys Ser Asp Leu Glu Glu Ser Lys Glu Trp Ile Arg Arg Ser Asn Lys
            20                  25                  30

Ile Leu Asp Ser Ile Gly Ser Gly Ser Gly Cys Xaa
        35                  40

<210> SEQ ID NO 10
<211> LENGTH: 44
<212> TYPE: PRT
<213> ORGANISM: Artificial
<220> FEATURE:
<223> OTHER INFORMATION: VIKI-PEG4-palm peptide
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (44)..(44)
<223> OTHER INFORMATION: X at position 44 is (PEG4-palm)-NH2

<400> SEQUENCE: 10

Xaa Val Ala Leu Asp Pro Ile Asp Ile Ser Ile Val Leu Asn Lys Ile
1               5                   10                  15

Lys Ser Asp Leu Glu Glu Ser Lys Glu Trp Ile Arg Arg Ser Asn Lys
            20                  25                  30

Ile Leu Asp Ser Ile Gly Ser Gly Ser Gly Cys Xaa
        35                  40

<210> SEQ ID NO 11
<211> LENGTH: 44
<212> TYPE: PRT
<213> ORGANISM: Artificial
<220> FEATURE:
<223> OTHER INFORMATION: VIKI-PEG4-25OHchol peptide
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (44)..(44)
<223> OTHER INFORMATION: X at position 44 is (PEG4-25OHchol)-NH2

<400> SEQUENCE: 11

Xaa Val Ala Leu Asp Pro Ile Asp Ile Ser Ile Val Leu Asn Lys Ile
1               5                   10                  15

Lys Ser Asp Leu Glu Glu Ser Lys Glu Trp Ile Arg Arg Ser Asn Lys
            20                  25                  30

Ile Leu Asp Ser Ile Gly Ser Gly Ser Gly Cys Xaa
        35                  40
```

```
<210> SEQ ID NO 12
<211> LENGTH: 44
<212> TYPE: PRT
<213> ORGANISM: Artificial
<220> FEATURE:
<223> OTHER INFORMATION: VIKI-PEG4-C20 peptide
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (44)..(44)
<223> OTHER INFORMATION: X at position 44 is (PEG4-C20)-NH2

<400> SEQUENCE: 12

Xaa Val Ala Leu Asp Pro Ile Asp Ile Ser Ile Val Leu Asn Lys Ile
1               5                   10                  15

Lys Ser Asp Leu Glu Glu Ser Lys Glu Trp Ile Arg Arg Ser Asn Lys
            20                  25                  30

Ile Leu Asp Ser Ile Gly Ser Gly Ser Gly Cys Xaa
        35                  40

<210> SEQ ID NO 13
<211> LENGTH: 44
<212> TYPE: PRT
<213> ORGANISM: Artificial
<220> FEATURE:
<223> OTHER INFORMATION: VIKI-PEG4-C30 peptide
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (44)..(44)
<223> OTHER INFORMATION: X at position 44 is (PEG4-C30)-NH2

<400> SEQUENCE: 13

Xaa Val Ala Leu Asp Pro Ile Asp Ile Ser Ile Val Leu Asn Lys Ile
1               5                   10                  15

Lys Ser Asp Leu Glu Glu Ser Lys Glu Trp Ile Arg Arg Ser Asn Lys
            20                  25                  30

Ile Leu Asp Ser Ile Gly Ser Gly Ser Gly Cys Xaa
        35                  40

<210> SEQ ID NO 14
<211> LENGTH: 44
<212> TYPE: PRT
<213> ORGANISM: Artificial
<220> FEATURE:
<223> OTHER INFORMATION: VIKI-PEG4-Betulinic peptide
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (44)..(44)
<223> OTHER INFORMATION: X at position 44 is (PEG4-Betulinic)-NH2

<400> SEQUENCE: 14

Xaa Val Ala Leu Asp Pro Ile Asp Ile Ser Ile Val Leu Asn Lys Ile
1               5                   10                  15

Lys Ser Asp Leu Glu Glu Ser Lys Glu Trp Ile Arg Arg Ser Asn Lys
            20                  25                  30
```

Ile Leu Asp Ser Ile Gly Ser Gly Ser Gly Cys Xaa
            35                  40

<210> SEQ ID NO 15
<211> LENGTH: 44
<212> TYPE: PRT
<213> ORGANISM: Artificial
<220> FEATURE:
<223> OTHER INFORMATION: VIKI-PEG4-Ursolic peptide
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (44)..(44)
<223> OTHER INFORMATION: X at position 44 is (PEG4-Ursolic)-NH2

<400> SEQUENCE: 15

Xaa Val Ala Leu Asp Pro Ile Asp Ile Ser Ile Val Leu Asn Lys Ile
1               5                   10                  15

Lys Ser Asp Leu Glu Glu Ser Lys Glu Trp Ile Arg Arg Ser Asn Lys
            20                  25                  30

Ile Leu Asp Ser Ile Gly Ser Gly Ser Gly Cys Xaa
            35                  40

<210> SEQ ID NO 16
<211> LENGTH: 44
<212> TYPE: PRT
<213> ORGANISM: Artificial
<220> FEATURE:
<223> OTHER INFORMATION: VIKI-PEG24-chol peptide
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (44)..(44)
<223> OTHER INFORMATION: X at position 44 is (PEG24-chol)-NH2

<400> SEQUENCE: 16

Xaa Val Ala Leu Asp Pro Ile Asp Ile Ser Ile Val Leu Asn Lys Ile
1               5                   10                  15

Lys Ser Asp Leu Glu Glu Ser Lys Glu Trp Ile Arg Arg Ser Asn Lys
            20                  25                  30

Ile Leu Asp Ser Ile Gly Ser Gly Ser Gly Cys Xaa
            35                  40

<210> SEQ ID NO 17
<211> LENGTH: 44
<212> TYPE: PRT
<213> ORGANISM: Artificial
<220> FEATURE:
<223> OTHER INFORMATION: VIKI-PEG24-toc peptide
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (44)..(44)
<223> OTHER INFORMATION: X at position 44 is (PEG24-toc)-NH2

<400> SEQUENCE: 17

Xaa Val Ala Leu Asp Pro Ile Asp Ile Ser Ile Val Leu Asn Lys Ile
1               5                   10                  15

Lys Ser Asp Leu Glu Glu Ser Lys Glu Trp Ile Arg Arg Ser Asn Lys

```
Ile Leu Asp Ser Ile Gly Ser Gly Ser Gly Cys Xaa
        35                  40
```

<210> SEQ ID NO 18
<211> LENGTH: 44
<212> TYPE: PRT
<213> ORGANISM: Artificial
<220> FEATURE:
<223> OTHER INFORMATION: VIQKI-PEG24-chol peptide
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (44)..(44)
<223> OTHER INFORMATION: X at position 44 is (PEG24-chol)-NH2

<400> SEQUENCE: 18

```
Xaa Val Ala Leu Asp Pro Ile Asp Ile Ser Ile Val Leu Asn Lys Ile
1               5                   10                  15

Lys Ser Gln Leu Glu Glu Ser Lys Glu Trp Ile Arg Arg Ser Asn Lys
            20                  25                  30

Ile Leu Asp Ser Ile Gly Ser Gly Ser Gly Cys Xaa
        35                  40
```

Gln Ile Ile His Asp Phe Val Asp Lys Gly Ser Gly Ser Gly Cys Xaa
            20                  25                  30

<210> SEQ ID NO 21
<211> LENGTH: 31
<212> TYPE: PRT
<213> ORGANISM: Artificial
<220> FEATURE:
<223> OTHER INFORMATION: Viral peptide inhibitor EBOLA-dPEG4
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (31)..(31)
<223> OTHER INFORMATION: X at position 31 is dPEG4-C-NH2

<400> SEQUENCE: 21

Xaa Ile Glu Pro His Asp Trp Thr Lys Asn Ile Thr Asp Lys Ile Asp
1               5                   10                  15

Gln Ile Ile His Asp Phe Val Asp Lys Gly Ser Gly Ser Gly Xaa
            20                  25                  30

<210> SEQ ID NO 22
<211> LENGTH: 31
<212> TYPE: PRT
<213> ORGANISM: Artificial
<220> FEATURE:
<223> OTHER INFORMATION: Viral peptide inhibitor EBOLA-dPEG4-Chol
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (31)..(31)
<223> OTHER INFORMATION: X at position 31 is dPEG4-C-(Cholesterol)

<400> SEQUENCE: 22

Xaa Ile Glu Pro His Asp Trp Thr Lys Asn Ile Thr Asp Lys Ile Asp
1               5                   10                  15

Gln Ile Ile His Asp Phe Val Asp Lys Gly Ser Gly Ser Gly Xaa
            20                  25                  30

<210> SEQ ID NO 23
<211> LENGTH: 31
<212> TYPE: PRT
<213> ORGANISM: Artificial
<220> FEATURE:
<223> OTHER INFORMATION: Viral peptide inhibitor EBOLA-dPEG4-Toc
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (31)..(31)
<223> OTHER INFORMATION: X at position 31 is dPEG4-C-(Tocopherol)

<400> SEQUENCE: 23

Xaa Ile Glu Pro His Asp Trp Thr Lys Asn Ile Thr Asp Lys Ile Asp
1               5                   10                  15

Gln Ile Ile His Asp Phe Val Asp Lys Gly Ser Gly Ser Gly Xaa
            20                  25                  30

<210> SEQ ID NO 24
<211> LENGTH: 46

```
<212> TYPE: PRT
<213> ORGANISM: Artificial
<220> FEATURE:
<223> OTHER INFORMATION: Viral peptide inhibitor TAT-EBOLA
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (46)..(46)
<223> OTHER INFORMATION: X at position 46 is NH2

<400> SEQUENCE: 24

Xaa Tyr Gly Arg Lys Lys Arg Arg Gln Arg Arg Gly Ser Gly Ile
1               5                   10                  15

Glu Pro His Asp Trp Thr Lys Asn Ile Thr Asp Lys Ile Asp Gln Ile
            20                  25                  30

Ile His Asp Phe Val Asp Lys Gly Ser Gly Ser Gly Cys Xaa
        35                  40                  45

<210> SEQ ID NO 25
<211> LENGTH: 45
<212> TYPE: PRT
<213> ORGANISM: Artificial
<220> FEATURE:
<223> OTHER INFORMATION: Viral peptide inhibitor TAT-EBOLA-dPEG4
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (45)..(45)
<223> OTHER INFORMATION: X at position 45 is dPEG4-C-NH2

<400> SEQUENCE: 25

Xaa Tyr Gly Arg Lys Lys Arg Arg Gln Arg Arg Gly Ser Gly Ile
1               5                   10                  15

Glu Pro His Asp Trp Thr Lys Asn Ile Thr Asp Lys Ile Asp Gln Ile
            20                  25                  30

Ile His Asp Phe Val Asp Lys Gly Ser Gly Ser Gly Xaa
        35                  40                  45

<210> SEQ ID NO 26
<211> LENGTH: 45
<212> TYPE: PRT
<213> ORGANISM: Artificial
<220> FEATURE:
<223> OTHER INFORMATION: Viral peptide inhibitor TAT-EBOLA-dPEG4-Chol
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (45)..(45)
<223> OTHER INFORMATION: X at position 45 is dPEG4-C-(Cholesterol)

<400> SEQUENCE: 26

Xaa Tyr Gly Arg Lys Lys Arg Arg Gln Arg Arg Gly Ser Gly Ile
1               5                   10                  15

Glu Pro His Asp Trp Thr Lys Asn Ile Thr Asp Lys Ile Asp Gln Ile
            20                  25                  30

Ile His Asp Phe Val Asp Lys Gly Ser Gly Ser Gly Xaa
        35                  40                  45
```

```
<210> SEQ ID NO 27
<211> LENGTH: 45
<212> TYPE: PRT
<213> ORGANISM: Artificial
<220> FEATURE:
<223> OTHER INFORMATION: Viral peptide inhibitor TAT-EBOLA-dPEG4-Toc
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (45)..(45)
<223> OTHER INFORMATION: X at position 45 is dPEG4-C-(Tocopherol)

<400> SEQUENCE: 27

Xaa Tyr Gly Arg Lys Lys Arg Arg Gln Arg Arg Gly Ser Gly Ile
1               5                   10                  15

Glu Pro His Asp Trp Thr Lys Asn Ile Thr Asp Lys Ile Asp Gln Ile
                20                  25                  30

Ile His Asp Phe Val Asp Lys Gly Ser Gly Ser Gly Xaa
            35                  40                  45

<210> SEQ ID NO 28
<211> LENGTH: 52
<212> TYPE: PRT
<213> ORGANISM: Artificial
<220> FEATURE:
<223> OTHER INFORMATION: Viral peptide inhibitor TAT-HPIV3-dPEG4
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (52)..(52)
<223> OTHER INFORMATION: X at position 52 is dPEG4-C-NH2

<400> SEQUENCE: 28

Xaa Tyr Gly Arg Lys Lys Arg Arg Gln Arg Arg Gly Ser Gly Val
1               5                   10                  15

Ala Leu Asp Pro Ile Asp Ile Ser Ile Val Leu Asn Lys Ala Lys Ser
                20                  25                  30

Asp Leu Glu Glu Ser Lys Glu Trp Ile Arg Arg Ser Asn Gly Lys Leu
            35                  40                  45

Asp Ser Ile Xaa
        50

<210> SEQ ID NO 29
<211> LENGTH: 52
<212> TYPE: PRT
<213> ORGANISM: Artificial
<220> FEATURE:
<223> OTHER INFORMATION: Viral peptide inhibitor TAT-HPIV3-dPEG4-Chol
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (52)..(52)
<223> OTHER INFORMATION: X at position 52 is dPEG4-C-(Cholesterol)

<400> SEQUENCE: 29

Xaa Tyr Gly Arg Lys Lys Arg Arg Gln Arg Arg Gly Ser Gly Val
1               5                   10                  15

Ala Leu Asp Pro Ile Asp Ile Ser Ile Val Leu Asn Lys Ala Lys Ser
                20                  25                  30
```

```
Asp Leu Glu Glu Ser Lys Glu Trp Ile Arg Arg Ser Asn Gly Lys Leu
        35                  40                  45

Asp Ser Ile Xaa
    50

<210> SEQ ID NO 30
<211> LENGTH: 52
<212> TYPE: PRT
<213> ORGANISM: Artificial
<220> FEATURE:
<223> OTHER INFORMATION: Viral peptide inhibitor TAT-HPIV3-dPEG4-Toc
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (52)..(52)
<223> OTHER INFORMATION: X at position 52 is dPEG4-C-(Tocopherol)

<400> SEQUENCE: 30

Xaa Tyr Gly Arg Lys Lys Arg Arg Gln Arg Arg Gly Ser Gly Val
1               5                   10                  15

Ala Leu Asp Pro Ile Asp Ile Ser Ile Val Leu Asn Lys Ala Lys Ser
            20                  25                  30

Asp Leu Glu Glu Ser Lys Glu Trp Ile Arg Arg Ser Asn Gly Lys Leu
        35                  40                  45

Asp Ser Ile Xaa
    50

<210> SEQ ID NO 31
<211> LENGTH: 40
<212> TYPE: PRT
<213> ORGANISM: Artificial
<220> FEATURE:
<223> OTHER INFORMATION: Viral peptide inhibitor C105-EBOLA-dPEG4
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (40)..(40)
<223> OTHER INFORMATION: X at position 40 is dPEG4-C-NH2

<400> SEQUENCE: 31

Xaa Pro Phe Val Tyr Leu Ile Gly Ser Gly Ile Glu Pro His Asp Trp
1               5                   10                  15

Thr Lys Asn Ile Thr Asp Lys Ile Asp Gln Ile Ile His Asp Phe Val
            20                  25                  30

Asp Lys Gly Ser Gly Ser Gly Xaa
        35                  40

<210> SEQ ID NO 32
<211> LENGTH: 40
<212> TYPE: PRT
<213> ORGANISM: Artificial
<220> FEATURE:
<223> OTHER INFORMATION: Viral peptide inhibitor  C105-EBOLA-dPEG4-Chol
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (40)..(40)
<223> OTHER INFORMATION: X at position 40 is dPEG4-C-(Cholesterol)
```

<400> SEQUENCE: 32

Xaa Pro Phe Val Tyr Leu Ile Gly Ser Gly Ile Glu Pro His Asp Trp
1               5                   10                  15

Thr Lys Asn Ile Thr Asp Lys Ile Asp Gln Ile Ile His Asp Phe Val
            20                  25                  30

Asp Lys Gly Ser Gly Ser Gly Xaa
        35                  40

<210> SEQ ID NO 33
<211> LENGTH: 40
<212> TYPE: PRT
<213> ORGANISM: Artificial
<220> FEATURE:
<223> OTHER INFORMATION: Viral peptide inhibitor C105-EBOLA-dPEG4-Toc
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (40)..(40)
<223> OTHER INFORMATION: X at position 40 is dPEG4-C-(Tocopherol)

<400> SEQUENCE: 33

Xaa Pro Phe Val Tyr Leu Ile Gly Ser Gly Ile Glu Pro His Asp Trp
1               5                   10                  15

Thr Lys Asn Ile Thr Asp Lys Ile Asp Gln Ile Ile His Asp Phe Val
            20                  25                  30

Asp Lys Gly Ser Gly Ser Gly Xaa
        35                  40

<210> SEQ ID NO 34
<211> LENGTH: 43
<212> TYPE: PRT
<213> ORGANISM: Artificial
<220> FEATURE:
<223> OTHER INFORMATION: Viral peptide inhibitor FIV-dPEG4-Chol
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE
<222> LOCATION: (43)..(43)
<223> OTHER INFORMATION: X at position 43 is dPEG4-C-(Cholesterol)

<400> SEQUENCE: 34

Xaa Trp Tyr Asn Gln Thr Lys Asp Leu Gln Gln Lys Phe Tyr Glu Ile
1               5                   10                  15

Ile Met Asp Ile Ile Glu Gln Asn Asn Val Gln Gly Lys Lys Gly Ile
            20                  25                  30

Gln Gln Leu Gln Lys Gly Ser Gly Ser Gly Xaa
        35                  40

<210> SEQ ID NO 35
<211> LENGTH: 43
<212> TYPE: PRT
<213> ORGANISM: Artificial
<220> FEATURE:
<223> OTHER INFORMATION: Viral peptide inhibitor FIV-dPEG4-Toc
<220> FEATURE:
<221> NAME/KEY: MISC_FEATURE
<222> LOCATION: (1)..(1)
<223> OTHER INFORMATION: X at position 1 is an acetyl group
<220> FEATURE:
<221> NAME/KEY: MISC_FEATURE

```
<222> LOCATION: (43)..(43)
<223> OTHER INFORMATION: X at position 43 is dPEG4-C-(Tocopherol)

<400> SEQUENCE: 35

Xaa Trp Tyr Asn Gln Thr Lys Asp Leu Gln Gln Lys Phe Tyr Glu Ile
1               5                   10                  15

Ile Met Asp Ile Ile Glu Gln Asn Asn Val Gln Gly Lys Lys Gly Ile
            20                  25                  30

Gln Gln Leu Gln Lys Gly Ser Gly Ser Gly Xaa
        35                  40

<210> SEQ ID NO 36
<211> LENGTH: 24
<212> TYPE: PRT
<213> ORGANISM: Artificial
<220> FEATURE:
<223> OTHER INFORMATION: C-terminal heptad repeat region of Zaire Ebola
      GP2 610-633

<400> SEQUENCE: 36

Ile Glu Pro His Asp Trp Thr Lys Asn Ile Thr Asp Lys Ile Asp Gln
1               5                   10                  15

Ile Ile His Asp Phe Val Asp Lys
            20

<210> SEQ ID NO 37
<211> LENGTH: 24
<212> TYPE: PRT
<213> ORGANISM: Artificial
<220> FEATURE:
<223> OTHER INFORMATION: C-terminal heptad repeat region of Marburg Lake
      Victoria-Musoke

<400> SEQUENCE: 37

Ile Gly Ile Glu Asp Leu Ser Lys Asn Ile Ser Glu Gln Ile Asp Gln
1               5                   10                  15

Ile Lys Lys Asp Glu Gln Lys Glu
            20

<210> SEQ ID NO 38
<211> LENGTH: 36
<212> TYPE: PRT
<213> ORGANISM: Artificial
<220> FEATURE:
<223> OTHER INFORMATION: Measles Virus HRC1 peptide derived from
      C-terminal heptad repeat region

<400> SEQUENCE: 38

Pro Pro Ile Ser Leu Glu Arg Leu Asp Val Gly Thr Asn Leu Gly Asn
1               5                   10                  15

Ala Ile Ala Lys Leu Glu Asp Ala Lys Glu Leu Leu Glu Ser Ser Asp
            20                  25                  30

Gln Ile Leu Arg
        35
```